(12) United States Patent
Endo

(10) Patent No.: US 11,452,762 B2
(45) Date of Patent: *Sep. 27, 2022

(54) METHOD OF TREATING RHINITIS WITH C-TYPE NATRIURETIC PEPTIDES

(71) Applicants: IGISU Co., Ltd., Tokyo (JP); Yori Endo, Sendai (JP); Kyoko Endo, Tokyo (JP)

(72) Inventor: Kyoko Endo, Sendai (JP)

(73) Assignees: Igisu Co., Ltd., Tokyo (JP); Yori Endo, Sendai (JP); Kyoko Endo, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/939,622

(22) Filed: Mar. 29, 2018

(65) Prior Publication Data

US 2018/0318395 A1    Nov. 8, 2018

Related U.S. Application Data

(63) Continuation of application No. 15/160,268, filed on May 20, 2016, now Pat. No. 9,962,429, which is a continuation of application No. 14/193,017, filed on Feb. 28, 2014, now Pat. No. 9,358,270, which is a continuation of application No. 13/392,657, filed as application No. PCT/JP2010/064644 on Aug. 27, 2010, now abandoned.

(30) Foreign Application Priority Data

Aug. 27, 2009   (JP) ................................ 2009-197488

(51) Int. Cl.
  *A61K 38/22*   (2006.01)
  *A61K 9/00*    (2006.01)

(52) U.S. Cl.
  CPC ............ *A61K 38/22* (2013.01); *A61K 9/0043* (2013.01); *A61K 38/2242* (2013.01)

(58) Field of Classification Search
  None
  See application file for complete search history.

(56) References Cited

U.S. PATENT DOCUMENTS

| | | | |
|---|---|---|---|
| 5,114,923 A | 5/1992 | Seilhamer et al. |
| 5,434,133 A | 7/1995 | Tanaka et al. |
| 5,583,108 A | 12/1996 | Chi-Ming et al. |
| 5,674,710 A | 10/1997 | Seilhamer et al. |
| 6,028,055 A | 2/2000 | Lowe et al. |
| 6,707,211 B2 | 3/2004 | Oohashi et al. |
| 6,818,619 B2 | 11/2004 | Burnett, Jr. et al. |
| 7,384,917 B2 | 6/2008 | Burnett, Jr. et al. |
| 8,198,242 B2 | 6/2012 | Wendt et al. |
| 8,354,496 B2 | 1/2013 | Pan et al. |
| 8,455,438 B2 | 6/2013 | Burnett, Jr. et al. |
| 8,642,550 B2 | 2/2014 | Dickey et al. |
| 9,358,270 B2 | 6/2016 | Endo |
| 9,962,429 B2 | 5/2018 | Endo |
| 2007/0197434 A1 | 8/2007 | Nakao et al. |
| 2008/0070858 A1 | 3/2008 | Mohapatra |
| 2008/0312142 A1 | 12/2008 | Nakao et al. |
| 2013/0045921 A1 | 2/2013 | Endo |

FOREIGN PATENT DOCUMENTS

| | | |
|---|---|---|
| DE | 102004048576 A1 | 4/2006 |
| EP | 0497368 A1 | 8/1992 |
| EP | 1118329 A1 | 7/2001 |
| EP | 1743653 A1 | 1/2007 |
| EP | 1810716 A1 | 7/2007 |
| EP | 2308889 A1 | 4/2011 |
| JP | 05-207891 A1 | 8/1993 |
| JP | 06-009688 A | 1/1994 |
| JP | 2000-169387 A | 6/2000 |
| JP | 2007-525213 A | 9/2007 |
| JP | 2007-525957 A | 9/2007 |
| JP | 2008-509746 A | 4/2008 |
| JP | 2008-162987 A | 7/2008 |
| JP | 2008-540509 A | 11/2008 |
| JP | 2010-500032 A1 | 1/2010 |
| JP | 2010-539022 A | 12/2010 |
| WO | WO 1998/52599 A1 | 11/1998 |
| WO | WO 2004/022003 A2 | 3/2004 |
| WO | WO 2004/110489 A1 | 12/2004 |
| WO | WO 2005/072055 A2 | 8/2005 |
| WO | WO 2005/094889 A1 | 10/2005 |
| WO | WO 2005/094890 A1 | 10/2005 |
| WO | WO 2006/020841 A2 | 2/2006 |
| WO | WO 2007/023396 A2 | 3/2007 |

(Continued)

OTHER PUBLICATIONS

Extended European Search Report for European Application No. 10812022.1 dated Jan. 17, 2013.
International Search Report for PCT/JP2010/064644, dated Oct. 12, 2010.
Australian Office Action dated Sep. 4, 2012 in connection with Australian Application No. 2010287421.
Russian Office Action dated Jan. 18, 2013 in connection with Russian Application No. 2012105046/15(007659) and its English translation thereof.

(Continued)

*Primary Examiner* — Elly-Gerald Stoica
(74) *Attorney, Agent, or Firm* — Wolf, Greenfield & Sacks, P.C.

(57) ABSTRACT

The problem to be solved by the present invention is to provide an effective and safe therapeutic preparation for rhinitis, which not only has significant effects on improvement in rhinitis, in particular allergic rhinitis, but also is rapid in manifestation of efficacy, fast-acting, and long-lasting, without local side effects.

Means for solving the problem is a therapeutic preparation for rhinitis, in particular allergic rhinitis, comprising C-type natriuretic peptide (CNP) or B-type natriuretic peptide (BNP) as the active ingredient.

18 Claims, 1 Drawing Sheet
Specification includes a Sequence Listing.

(56) References Cited

FOREIGN PATENT DOCUMENTS

| WO | WO 2008/021872 A1 | 2/2008 |
| WO | WO 2008/031045 A2 | 3/2008 |
| WO | WO 2008/032450 A1 | 3/2008 |
| WO | WO 2008/133349 A1 | 11/2008 |
| WO | WO 2008/140125 A1 | 11/2008 |
| WO | WO 2009/033701 A1 | 3/2009 |
| WO | WO 2009/033807 A2 | 3/2009 |
| WO | WO 2009/046861 A1 | 4/2009 |
| WO | WO 2009/067639 A2 | 5/2009 |

OTHER PUBLICATIONS

UniProtKB/Swiss-Prot Submission; Accession No. P23582; Tawaragi et al.; Nov. 1, 1991.

UniProtKB/Swiss-Prot Submission; Accession No. P07634; Maekawa et al.; Jul. 1, 1989.

UniProtKB/Swiss-Prot Submission; Accession No. P13205; Kojima et al.; Feb. 1, 1991.

UniProtKB/Swiss-Prot Submission; Accession No. P40753; Ogawa et al.; Nov. 1, 1995.

[No Author Listed] B-type natriuretic peptide. Feb. 25, 2015. 5 pages.

Agoston et al., Dexamethasone stimulates expression of C-type Natriuretic Peptide in chondrocytes, *BMC Musculoskeletal Disorders*, 2006, 7: 87.

Chiurchiù et al., Brain Natriuretic Peptide (BNP) regulates the production of inflammatory mediators in human THP-1 macrophages, *Regulatory Peptides*, 2008, 148: 26-32.

Chusho et al., Dwarfism and early death in mice lacking C-type natriuretic peptide, Proceedings of the National Academy of Sciences of the US, 2001, 98(7): 4016-4021.

Kiemer et al. The atrial natriuretic peptide regulates the production of inflammatory mediators in macrophages, Annals of the Rheumatic Disease, 2001, 60: 68-70.

Kumar et al., Atrial natriuretic peptide gene transfer by means of intranasal administration attenuates airway reactivity in a mouse model of allergic sensitization. J Allergy Clinical Immunol. 2002;110:879-82.

Kuroski De Bold et al., Cardiac hormones ANF and BNP modulate proliferation in the unidirectional mixed lymphocyte reaction, The Journal of Heart and Lung Transplantation, 2010, 29(3): 323-326.

Meirovich et al., Relationship Between Natriuretic Peptides and Inflammation: Proteomic Evidence Obtained During Acute Cellular Cardia Allograft Rejection in Humans, The Journal of Heart and Lung Transplantation, 2008, 27: 31-37.

Mohaptra et al., Intranasal atrial natriuretic peptide (ANP) gene transfer attenuates airway reactivity in a mouse model of allergic asthma. J Allergy Clinical Immunol. 2003;111:S309. Abstract #962.

Obata et al., CNP infusion attenuates cardiac dysfunction and inflammation in myocarditis, 2007, Biochem. Biophys. Res. Commun., 2007, 356: 60-66.

Ogawa et al., Human C-type natriuretic peptide. Characterization of the gene and peptide. Hypertension. Jun. 1992;19(6 Pt 2):809-13.

Pawankar et al., Overview on the pathomechanisms of allergic rhinitis. Asia Pac Allergy. Oct. 2011;1(3):157-67. Epub Oct. 11, 2011.

Porter et al., Cloning of a cDNA encoding porcine brain natriuretic peptide. J Biol Chem. Apr. 25, 1989;264(12):6689-92.

Reichert et al., Molecular and physiological effects of nesiritide, Can. J. Cardiol., 2008, pp. 15B-18B, vol. 24, Suppl. B.

Scotland, R. et al., C-type natriuretic peptide inhibits leukocyte recruitment and platelet-leukocyte interactions via suppression of P-selectin expression, Proc. Natl. Acad. Sci. USA, 2005, 102(40): 14452-14457.

Steinhelper, Structure, expression, and genomic mapping of the mouse natriuretic peptide type-B gene. Circ Res. May 1993;72(5):984-92.

Tomoda et al., C-type natriuretic peptide is synthesized and secreted from leukemia cell lines, peripheral blood cells, and peritoneal macrophages, Experimental Hematology, 2001, 29: 609-615.

Yoshibayashi et al., Brain natriuretic peptide versus atrial natriuretic peptide-physiological and pathophysiological significance in children and adults: a review, European Journal of Endocrinology, 1996, 135: 265-268.

[Fig. 1]
```
Human BNP peptide    SPKMVQGSGCFGRKMDRISSSSGLGCKVLRRH
Human CNP peptide    ----GLSKGCFGLKLDRIGSMSGLGC------
Human ANP peptide    ---SLRRSSCFGGRMDRIGAQSGLGCNSFRY-
```
[Fig. 2]
Therapeutic effects on rhinitis of 100 μg/ml CNP nasal drop preparations
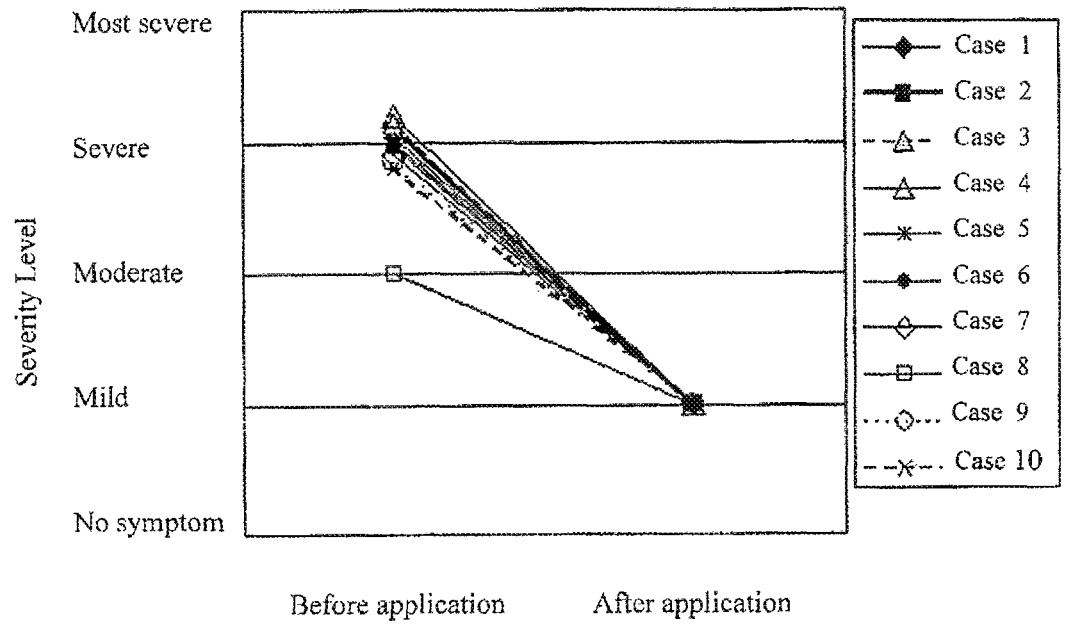
[Fig. 3]
Therapeutic effects on rhinitis of BNP nasal drop preparations
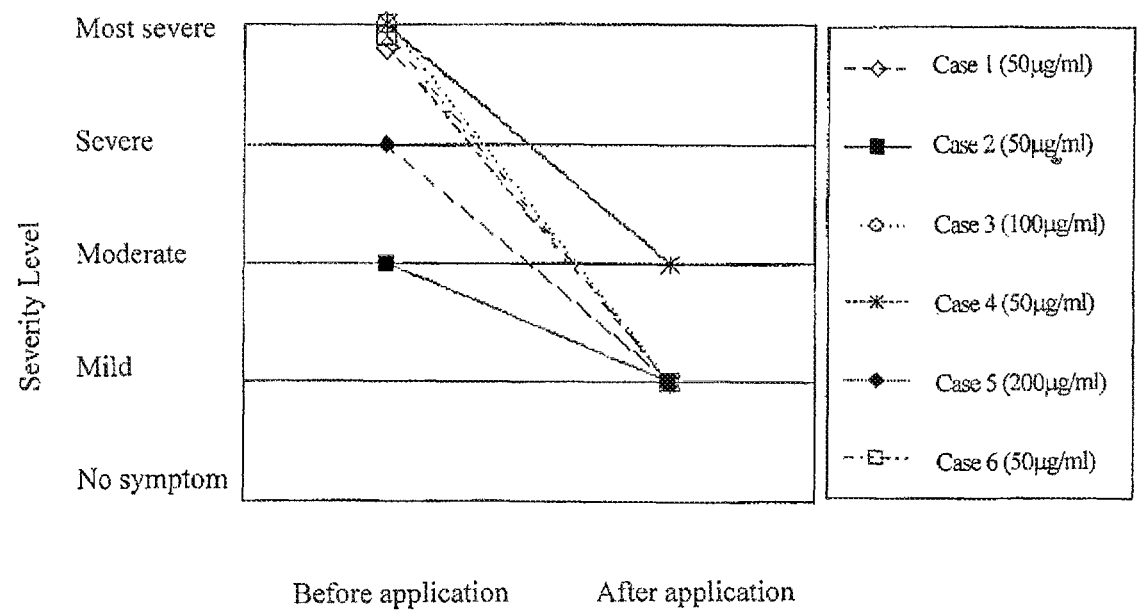

SEQUENCE LISTING

```
<160> NUMBER OF SEQ ID NOS: 25

<210> SEQ ID NO 1
<211> LENGTH: 22
<212> TYPE: PRT
<213> ORGANISM: Homo sapiens

<400> SEQUENCE: 1

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 2
<211> LENGTH: 32
<212> TYPE: PRT
<213> ORGANISM: Homo sapiens

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 3
<211> LENGTH: 26
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 3

Ser Pro Lys Met Val Gln Gly Ser Gly Cys Phe Gly Arg Lys Met Asp
1               5                   10                  15

Arg Ile Ser Ser Ser Ser Gly Leu Gly Cys
            20                  25

<210> SEQ ID NO 4
<211> LENGTH: 32
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 4

Ser Pro Lys Met Val Gln Gly Ser Gly Cys Phe Gly Arg Lys Met Asp
1               5                   10                  15

Arg Ile Gly Ser Met Ser Gly Leu Gly Cys Lys Val Leu Arg Arg His
            20                  25                  30

<210> SEQ ID NO 5
<211> LENGTH: 26
```

-continued

```
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 5

Ser Pro Lys Met Val Gln Gly Ser Gly Cys Phe Gly Arg Lys Met Asp
1               5                   10                  15

Arg Ile Gly Ser Met Ser Gly Leu Gly Cys
            20                  25

<210> SEQ ID NO 6
<211> LENGTH: 32
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 6

Ser Pro Lys Met Val Gln Gly Ser Gly Cys Phe Gly Leu Lys Leu Asp
1               5                   10                  15

Arg Ile Ser Ser Ser Ser Gly Leu Gly Cys Lys Val Leu Arg Arg His
            20                  25                  30

<210> SEQ ID NO 7
<211> LENGTH: 26
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 7

Ser Pro Lys Met Val Gln Gly Ser Gly Cys Phe Gly Leu Lys Leu Asp
1               5                   10                  15

Arg Ile Ser Ser Ser Ser Gly Leu Gly Cys
            20                  25

<210> SEQ ID NO 8
<211> LENGTH: 32
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 8

Ser Pro Lys Met Val Gln Gly Ser Gly Cys Phe Gly Leu Lys Leu Asp
1               5                   10                  15

Arg Ile Gly Ser Met Ser Gly Leu Gly Cys Lys Val Leu Arg Arg His
            20                  25                  30

<210> SEQ ID NO 9
<211> LENGTH: 26
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 9

Ser Pro Lys Met Val Gln Gly Ser Gly Cys Phe Gly Leu Lys Leu Asp
1               5                   10                  15
```

Arg Ile Gly Ser Met Ser Gly Leu Gly Cys
            20                  25

<210> SEQ ID NO 10
<211> LENGTH: 28
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 10

Gly Leu Ser Lys Gly Cys Phe Gly Arg Lys Met Asp Arg Ile Ser Ser
1               5                   10                  15

Ser Ser Gly Leu Gly Cys Lys Val Leu Arg Arg His
            20                  25

<210> SEQ ID NO 11
<211> LENGTH: 22
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 11

Gly Leu Ser Lys Gly Cys Phe Gly Arg Lys Met Asp Arg Ile Ser Ser
1               5                   10                  15

Ser Ser Gly Leu Gly Cys
            20

<210> SEQ ID NO 12
<211> LENGTH: 28
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 12

Gly Leu Ser Lys Gly Cys Phe Gly Arg Lys Met Asp Arg Ile Gly Ser
1               5                   10                  15

Met Ser Gly Leu Gly Cys Lys Val Leu Arg Arg His
            20                  25

<210> SEQ ID NO 13
<211> LENGTH: 22
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 13

Gly Leu Ser Lys Gly Cys Phe Gly Arg Lys Met Asp Arg Ile Gly Ser
1               5                   10                  15

Met Ser Gly Leu Gly Cys
            20

<210> SEQ ID NO 14
<211> LENGTH: 28
<212> TYPE: PRT
<213> ORGANISM: Artificial Sequence
<220> FEATURE:
<223> OTHER INFORMATION: A chimeric peptide of human CNP peptide and
      human BNP peptide.

```
<400> SEQUENCE: 14

Gly Leu Ser Lys Gly Cys Phe Gly Leu Lys Leu Asp Arg Ile Ser Ser
1               5                   10                  15

Ser Ser Gly Leu Gly Cys Lys Val Leu Arg Arg His
            20                  25

<210> SEQ ID NO 15
<211> LENGTH: 22
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 15

Gly Leu Ser Lys Gly Cys Phe Gly Leu Lys Leu Asp Arg Ile Ser Ser
1               5                   10                  15

Ser Ser Gly Leu Gly Cys
            20

<210> SEQ ID NO 16
<211> LENGTH: 28
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 16

Gly Leu Ser Lys Gly Cys Phe Gly Leu Lys Leu Asp Arg Ile Gly Ser
1               5                   10                  15

Met Ser Gly Leu Gly Cys Lys Val Leu Arg Arg His
            20                  25

<210> SEQ ID NO 17
<211> LENGTH: 33
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 17

Arg Met Asp Arg Ile Gly Leu Ser Lys Gly Cys Phe Gly Leu Lys Leu
1               5                   10                  15

Asp Arg Ile Arg Glu Ala Ser Gly Leu Gly Cys Lys Val Leu Arg Arg
            20                  25                  30

His

<210> SEQ ID NO 18
<211> LENGTH: 33
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 18

Arg Met Asp Arg Ile Gly Leu Ser Lys Gly Cys Phe Gly Leu Lys Leu
1               5                   10                  15

Asp Arg Ile Gly Ser Met Ser Gly Leu Gly Cys Lys Val Leu Arg Arg
            20                  25                  30
```

His

```
<210> SEQ ID NO 19
<211> LENGTH: 28
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 19

Gly Leu Ser Lys Gly Cys Phe Gly Leu Lys Leu Asp Arg Ile Arg Glu
1               5                   10                  15

Ala Ser Gly Leu Gly Cys Lys Val Leu Arg Arg His
            20                  25

<210> SEQ ID NO 20
<211> LENGTH: 28
<212> TYPE: PRT
<213> ORGANISM: Artificial Sequence
<220> FEATURE:
<223> OTHER INFORMATION: A chimeric peptide of human CNP peptide and
      human BNP peptide.

<400> SEQUENCE: 20

Gly Leu Ser Lys Gly Cys Phe Gly Leu Lys Leu Asp Arg Ile Gly Ser
1               5                   10                  15

Met Ser Gly Leu Gly Cys Lys Val Leu Arg Arg His
            20                  25

<210> SEQ ID NO 21
<211> LENGTH: 5
<212> TYPE: PRT
<213> ORGANISM: Homo sapiens
<220> FEATURE:
<223> OTHER INFORMATION: A partial amino acid sequence in human CNP
      peptide and human BNP peptide.

<400> SEQUENCE: 21

Ser Gly Leu Gly Cys
1               5

<210> SEQ ID NO 22
<211> LENGTH: 53
<212> TYPE: PRT
<213> ORGANISM: Homo sapiens

<400> SEQUENCE: 22

Asp Leu Arg Val Asp Thr Lys Ser Arg Ala Ala Trp Ala Arg Leu Leu
1               5                   10                  15

Gln Glu His Pro Asn Ala Arg Lys Tyr Lys Gly Ala Asn Lys Lys Gly
            20                  25                  30

Leu Ser Lys Gly Cys Phe Gly Leu Lys Leu Asp Arg Ile Gly Ser Met
        35                  40                  45

Ser Gly Leu Gly Cys
        50

<210> SEQ ID NO 23
<211> LENGTH: 26
<212> TYPE: PRT
<213> ORGANISM: Homo sapiens

<400> SEQUENCE: 23

Met Val Gln Gly Ser Gly Cys Phe Gly Arg Lys Met Asp Arg Ile Ser
```

```
1               5                   10                  15
Ser Ser Ser Gly Leu Gly Cys Lys Val Leu
            20                  25
```

<210> SEQ ID NO 24
<211> LENGTH: 45
<212> TYPE: PRT
<213> ORGANISM: Rattus norvegicus

<400> SEQUENCE: 24

```
Ser Gln Gly Ser Thr Leu Arg Val Gln Gln Arg Pro Gln Asn Ser Lys
1               5                   10                  15

Val Thr His Ile Ser Ser Cys Phe Gly His Lys Ile Asp Arg Ile Gly
            20                  25                  30

Ser Val Ser Arg Leu Gly Cys Asn Ala Leu Lys Leu Leu
        35                  40              45
```

<210> SEQ ID NO 25
<211> LENGTH: 45
<212> TYPE: PRT
<213> ORGANISM: Mus musculus

<400> SEQUENCE: 25

```
Ser Gln Asp Ser Ala Phe Arg Ile Gln Glu Arg Leu Arg Asn Ser Lys
1               5                   10                  15

Met Ala His Ser Ser Cys Phe Gly Gln Lys Ile Asp Arg Ile Gly
            20                  25                  30

Ala Val Ser Arg Leu Gly Cys Asp Gly Leu Arg Leu Phe
        35                  40              45
```

METHOD OF TREATING RHINITIS WITH C-TYPE NATRIURETIC PEPTIDES

RELATED APPLICATION

This application is a continuation of U.S. application Ser. No. 15/160,268, filed May 20, 2016, which is a continuation of U.S. application Ser. No. 14/193,017, filed Feb. 28, 2014 and now U.S. Pat. No. 9,358,270, which is a continuation of U.S. application Ser. No. 13/392,657, filed Nov. 6, 2012, which is a national stage filing under 35 U.S.C. § 371 of international application PCT/JP2010/064644, filed Aug. 27, 2010, the entire disclosures of which are incorporated herein by reference.

TECHNICAL FIELD

The present invention relates to a therapeutic preparation for rhinitis comprising C-type natriuretic peptide (CNP) or B-type natriuretic peptide (BNP) as the active ingredient.

BACKGROUND ART

1. Rhinitis

Rhinitis refers to what is known as an inflammation of the so-called nasal mucous membrane, and histopathologically it is an exudative inflammation, often exhibited as pyogenic inflammation and allergic inflammation. In any cases, it is characterized by exudation of fluid components from the blood vessels, edema, cellular exudates and supersecretion.

Rhinitis includes various types such as acute rhinitis (so-called cold in the nose), chronic rhinitis, and allergic rhinitis depending on the cause and symptoms; usually, it is classified into four types depending on their causes and symptoms, namely infectious rhinitis, hypersensitive non-infectious rhinitis, irritant rhinitis, and others, as shown below.

TABLE 1

| 1. Infectious | (a) Acute rhinitis | | |
| | (b) Chronic rhinitis | | |
| 2. Hypersensitive non-infectious | (a) Combined type (hypersensitive nose) | (i) Allergic | Perennial allergic rhinitis |
| | | | Seasonal allergic rhinitis |
| | | (ii) Non-allergic | Vasomotor rhinitis (idiopathic rhinitis) |
| | | | Non-allergic rhinitis with eosinophilia syndrome |
| | (b) Rhinorrhea type | | Gustatory rhinitis |
| | | | Cold air inhalation-induced rhinitis |
| | | | Senile rhinitis |
| | (c) Congestive type | | Drug-induced rhinitis |
| | | | Psychogenic rhinitis |
| | | | Pregnancy rhinitis |
| | | | Endocrine rhinitis |
| | | | Cold-induced rhinitis |
| | (d) Dry type | | |
| 3. Irritant | (a) Physical irritant-induced rhinitis | | |
| | (b) Chemical irritant-induced rhinitis | | |
| | (c) Radiation-induced rhinitis | | |
| 4. Others | (a) Atrophic rhinitis | | |
| | (b) Specific granulomatous rhinitis | | |

Hereinafter, rhinitis of these types is explained.

Infectious rhinitis is classified into acute rhinitis (the so-called cold in the nose) which progresses within a short period, and chronic rhinitis which persists for along period. Infective chronic paranasal sinusitis, in which nasal cavities mainly around the ethmoid sinus and middle nasal meatus are affected, is also included in the infectious rhinitis.

Of the infectious rhinitis, most cases of the acute rhinitis are classified as a cold in the nose induced by infections mainly viral, but there are also many cases of acute simple rhinitis.

Symptoms of acute viral rhinitis (the cold) are characterized by runny nose, stuffy nose, and postnasal rhinorrhea in which nasal drip flows into the throat, coughing, slight fever and others. To relieve stuffy nose, vasoconstrictive agents such as spray-type nasal drop preparations of phenylephrine and oral medicines of pseudoephedrin are used. However, the use of such spray preparations must be limited to 3 to 4 days. When used for a longer period than this, the effectiveness of the medicine is reduced and a rebound phenomenon, in which the nasal mucous membranes become more congested than prior to the use, occurs. In addition, while antihistamine drugs have an effect to suppress runny nose, they also have side effects such as drowsiness.

In contrast, contributing factors of acute simple rhinitis include sinusitis, tonsillitis, and inflammation of adjacent organs such as the adenoids, as well as dust, soot, tobacco, air pollution, extreme temperature change, excessive dryness and moistness. Symptoms initiate with sneezing, and include excess rhinorrhea (nasal drip), nasal occlusion (stuffy nose), and impairment of the sense of smell; they resemble the symptoms of a cold of the nose, but do not include systemic symptoms such as fever. The nasal mucous membrane congests and swells. Disease is usually cured within 10 days, but occasionally bacterial infection occurs, worsening the symptoms and causing a fever. A prolonged course of the disease results in sinusitis or chronic rhinitis. For treatment, patients are rested and kept warm, and supportive measures are also taken, such as the use of antifebriles, analgesics, antitussive agents, and anti-inflammatory agents; when a bacterial infection occurs, antibiotics are used.

Chronic rhinitis is a long-term infectious rhinitis; when contributing factors of acute rhinitis are not improved, acute rhinitis turns into chronic rhinitis. Chronic rhinitis is often associated with chronic sinusitis. Chronic rhinitis has three pathological conditions, each referred to as chronic simple rhinitis, chronic hypertrophic rhinitis, and atrophic rhinitis.

Chronic simple rhinitis is a pathological condition in which the mucous membrane of the nasal cavities swells chronically due to repeated acute rhinitis. Symptoms of chronic simple rhinitis are mostly identical to those of hypertrophic rhinitis, and include nasal occlusion, excess rhinorrhea, impairment of the sense of smell and headache. However, it differs from chronic hypertrophic rhinitis in that swelling of the nasal mucous membrane is improved by vasoconstrictive agents. For treatment, removal of contributing factors is most important; conservative management such as the application of drugs and use of anti-inflammatory agents is also carried out.

Chronic hypertrophic rhinitis is caused by severe long-lasting inflammation. Chronic hypertrophic rhinitis is the most prevalent pathological condition among the chronic rhinitides, and exhibits severe swelling and thickening of the nasal mucous membrane.

Chronic atrophic rhinitis refers to a pathological condition wherein the mucous membrane of the nasal cavities and the bone tissues of the nose become atrophied, resulting in widened nasal cavities. Stuffy nose occurs on both sides and purulent nose drips are discharged. Discharges inside the nose attach to the wall of the nasal cavity in a crust like manner, releasing a bad odor.

Hypersensitive non-infectious rhinitis is a rhinitis wherein inflammation is caused by the mucous membrane of the nasal cavities that have become hypersensitive due to diathesis and some other reasons, so that it occurs by stimulations other than viruses and bacterial infection.

Furthermore, hypersensitive non-infectious rhinitis can be classified into combined-type rhinitis (hypersensitive nose), rhinorrhea-type rhinitis, congestive-type rhinitis, and dry-type rhinitis. In addition, combined-type rhinitis (hypersensitive nose) is further classified into allergic rhinitis and non-allergic rhinitis. Furthermore, allergic rhinitis can be classified into, from their favored onset timing, perennial allergic rhinitis and seasonal allergic rhinitis, and non-allergic rhinitis can be classified into vasomotor rhinitis (idiopathic rhinitis) and non-allergic rhinitis with eosinophilia syndrome. In addition, rhinorrhea-type rhinitis can be classified into gustatory rhinitis, cold air inhalation-induced rhinitis, and senile rhinitis; and congestive-type rhinitis can be classified into drug-induced rhinitis, psychogenic rhinitis, pregnancy rhinitis, and cold-induced rhinitis.

Combined-type rhinitis (hypersensitive nose) usually accompanies some of the symptoms including sneezing, watery rhinorrhea, and nasal occlusion (stuffy nose); for example, sneezing with watery rhinorrhea, sneezing with watery rhinorrhea and nasal occlusion.

Of the combined-type rhinitides (hypersensitive nose), allergic rhinitis is induced by the immune response of the body against causative substances in the external environment. Causative substances of allergic rhinitis generally include house dust, house dust mites, fungi, pollens, grasses, trees, and animals. More specifically, allergic rhinitis is a type-I allergic disease of the nasal mucous membrane, and is characterized by, in principle, paroxysmal repetitive sneezing, watery rhinorrhea, and nasal occlusion. Since allergic rhinitis is a type-I allergic disease, patients often have an allergic disposition (past history, complication, and family history of allergy), and are characterized by an increased serum level of specific IgE antibodies, increases in the local mast cells as well as local and blood eosinophils, and enhancement of non-specific sensitivity of the mucous membrane.

Of the allergic rhinitides, perennial allergic rhinitis is mostly caused by house dust and house dust mites, and seasonal allergic rhinitis is mostly caused by pollen.

Of the non-allergic rhinitides, vasomotor rhinitis (idiopathic rhinitis) is a kind of chronic rhinitis with some symptoms similar to those of general allergic rhinitis, i.e., nasal occlusion (stuffy nose), sneezing, and watery rhinorrhea (runny nose), but showing no apparent antigens. Symptoms include, in addition to stuffy nose, swelling of the mucous membrane with various colors from red to violet. Sometimes mild inflammation is observed in the paranasal sinuses. For treatment, anti-histamine drugs and anti-allergy agents are used.

Of the non-allergic rhinitides, non-allergic rhinitis with eosinophilia syndrome refers to a disease wherein an allergy test result is negative, but the amount of eosinophils in the nasal drip alone increases to some extent.

The rhinorrhea-type hypersensitive non-infectious rhinitis is characterized by rhinorrhea, and there are three types: gustatory rhinitis, cold air inhalation-induced rhinitis, and senile rhinitis. Gustatory rhinitis often occurs during eating highly-irritating foods or very hot foods. Cold air inhalation-induced rhinitis is a rhinorrhea induced by inhalation of cold air, which is famous as the skier's nose. Senile rhinitis is also characterized by watery rhinorrhea, but its cause is unknown.

Of the hypersensitive non-infectious rhinitides, congestive rhinitis is characterized by nasal occlusion as a predominant symptom, and is further classified into drug-induced rhinitis, psychogenic rhinitis, pregnancy rhinitis, endocrine rhinitis, and cold-induced rhinitis. Any of these types of rhinitis is characterized by congestion of the mucous membrane, and a stuffy nose is often observed.

Among them, drug-induced rhinitis is characterized by stuffy nose as a predominant symptom, which is reportedly possibly induced as a side effect of long-term continuous administration of drugs such as sympatholytic antihypertensive drugs, vasodilatory antihypertensive drugs, -stimulation antihypertensive drugs, bronchodilators, anti-depressants, and contraceptive pills. However, the most frequently observed cause is the abuse of a vasoconstrictor nasal drop preparation against nasal occlusion. Psychogenic rhinitis is observed with chronic stress, depression, and neurosis, and is characterized by nasal occlusion. Pregnancy rhinitis occurs in the second trimester or later of pregnancy, and its onset is considered to be particularly associated with actions of female hormone, especially estrogen, on the blood vessels of nasal mucous membranes and on autonomic receptors. Endocrine rhinitis is known with emphasis on a decrease in thyroid activity. But the number of the case is small. Cold-induced rhinitis is considered to be induced by reflex vasodilation in nasal mucosa, via cold stimulation of the body, in particular the hands and feet.

Of the hypersensitive non-infectious rhinitides, dry-type rhinitis (dry nose) is presumed to be induced as follows: when the humidity in a room becomes 20% or lower due to dry air and heating in winter, symptoms such as dry mucous membrane, crusting, and nasal bleeding occur, and hypersensitivity to irritation increases due to drying of the mucous layer, leading to nasal dryness and nasal occlusion sensations.

Irritant rhinitis is often caused by the working environment of an occupation, and is classified into physical irritant-induced rhinitis, chemical irritant-induced rhinitis and radiation-induced rhinitis based on the cause. Such physical irritant-induced rhinitis and chemical irritant-induced rhinitis develop by physical or chemical, acute or chronic irritation of mucous membranes. Inflammation is sometimes caused by radiation of nasal mucous membranes, which is called radiation-induced rhinitis.

Other types of rhinitis include atrophic rhinitis and specific granulomatous rhinitis. As symptoms of atrophic rhinitis (ozena), the nasal mucous membrane becomes thin and hard, and the nasal cavities extend to induce dryness; however, this type of rhinitis is currently rare in Japan. Specific granulomatous rhinitis is a rhinitis associated with granuloma, and includes specific rhinitis (tuberculosis, syphilis, etc.), sarcoidosis, and Wegener granulomatosis; however, the number of cases is extremely small.

In any case, rhinitis is a state of the nasal mucous membrane that is swelling by inflammation, characterized by symptoms such as runny nose and stuffy nose, which disturbs the daily lives of patients who experience difficulty in breathing; thus, rhinitis is a troublesome disease.

2. Treatment of Rhinitis

In the treatment of rhinitis, in particular allergic rhinitis, methods are generally selected based on the combination of severity level and disease type. The selection is not standardized, but according to "Guidelines for medical care of nasal allergies, 2009 edition" (edited by the committee for creation of guidelines for medical care of nasal allergies) treatment methods are as follows.

For mild cases, the first choice should be second-generation antihistamine drugs or chemical mediator releasing suppressants. When side effects such as drowsiness and dry mouth are not observed, first-generation antihistamine drugs having a fast-acting property may be administered.

In moderate cases, for sneezing/rhinorrhea type, one of the following:
(1) second-generation antihistamine drugs,
(2) chemical mediator releasing suppressants, or
(3) steroid nasal sprays,
is selected, and if necessary, either (1) or (2) is combined with (3).

In moderate cases, for nasal-occlusion type or mixed type with particularly severe nasal-occlusion cases, one of the following:
(1) anti-leukotriene drugs,
(2) anti-prostaglandin D2/thromboxane A2 drugs, or
(3) steroid nasal sprays,
is selected, and if necessary, either (1) or (2) is combined with (3).

In severe cases, when sneezing and rhinorrhea are particularly severe, a second-generation antihistamine drug is combined with a steroid nasal spray. Meanwhile, among severe cases of nasal-occlusion type or mixed type wherein nasal occlusion is particularly severe, an anti-leukotriene drug or anti-prostaglandin D2/thromboxane A2 drug is combined with a steroid nasal spray.

Attempts to remove and avoid antigens are required in any case; when sequential therapy is possible, application of specific immunotherapy is a choice, with which long-term remission can be expected. In cases of apparent morphological defects such as deviation of the nasal septum, or in cases wherein effects of drug therapy on nasal occlusion are insufficient, operative therapy is one choice of treatment. Effectiveness of antihistamine nasal sprays has been reported, but they are considered to be inferior to steroid nasal sprays.

As described above, representative treatments of allergic rhinitis include removal and a voidance of allergens, drug therapy, specific immunotherapy, and operative therapy; drugs used in the drug therapy can be classified into the following drug groups based on their action mechanism: steroids, histamine receptor antagonists, chemical mediator releasing suppressants, thromboxane A2 receptor antagonists, thromboxane A2 synthesis inhibitors, leukotriene antagonists, and Th2 cytokine inhibitors.

Among them, examples of steroids include beclomethasone (brand name: Beconase, Aldecin, Rhinocort, Salcoat), fluticasone (brand name: Flixonase), etc. Examples of histamine receptor antagonists include ketotifen (brand name: Zaditen), mequitazine (brand name: Zesulan), fexofenadine (brand name: Allegra), ebastine (brandname: Ebastel), bepotastine (brandname: Talion), olopatadine (brand name: Allelock), loratadine (brand name: Claritin), etc. Examples of chemical mediator releasing suppressants include cromolyn (brand name: Intal) and tranilast (brand name: Rizaben), etc. Examples of thromboxane A2 receptor antagonists include seratrodast (brand name: Bronica) and ramatroban (band name: Bynas), etc. Examples of thromboxane A2 synthesis inhibitors include ozagrel (brand name: Domenan or brand name: Vega), etc. Examples of leukotriene antagonists include montelukast (brandname: Singulair, Kipres) and pranlukast (brand name: Onon), etc. Examples of Th2 cytokine inhibitors include suplatast (brand name: IPD), etc.

Thus, while there are a number of drugs usable as therapeutic preparations for allergic rhinitis, steroids or histamine receptor antagonists are frequently used for moderate cases, and a combination of steroids and histamine receptor antagonists is used for severe cases.

Meanwhile, steroid nasal sprays elicit some local side effects such as nasal irritation, dryness, burning sensation of the nose, and nasal bleeding. In addition, when steroids are used for a long time, caution should be taken to avoid steroid withdrawal difficulty, and complications of infection should be a concern. There are a considerable number of cases of rhinitis that show resistance to steroid therapy. Furthermore, steroid nasal sprays do not have a long duration of effectiveness, and in the case of adult patients, application of about 4 times a day is necessary. Accordingly, many patients hesitate to use steroid nasal sprays, and there is a report stating that more than half of the patients did not take drugs in accordance with their prescription.

Furthermore, while antihistamine drugs suppress allergic reactions and their symptoms, they have disadvantages that they cause dryness in the nasal mucous membrane and drowsiness. In addition, while injection of allergens (hyposensitization therapy) leads to a long-term immunological tolerance against a specific causative substance, it takes from several months to several years for the manifestation of sufficient effects.

Under such circumstances, development of a novel therapeutic preparation for rhinitis that is not only efficacious and safe for patients with rhinitis, in particular patients with allergic rhinitis, but also has fewer local side effects without complication of infections, has been awaited. Moreover, development of a therapeutic preparation for rhinitis that is also efficacious for patients with severe cases who show treatment resistance to steroids has been awaited.

3. Natriuretic Peptides:

There are three known families of natriuretic peptides (NPs), named atrial natriuretic peptide (ANP), B-type natriuretic peptide (BNP), and C-type natriuretic peptide (CNP); their well-known members are composed of 28, 32, and 22 amino acid residues, respectively.

(1) ANP and BNP:

ANP and BNP are synthesized mainly by the atria and the ventricles, respectively, and released from the heart into the whole body. It is thought that nearly 100% of the circulating ANP and BNP in the blood originate from the heart. These ANP and BNP are reported to be deeply involved in a numerous diseases, including hypertension, cardiomegaly, cardiac failure, myocardial infarction, valvular heart disease, cardiac dysrhythmia, and pulmonary hypertension.

Human ANP is a peptide produced and released by atrial cardiocytes, and is composed of 28 amino acids, of which the $7^{th}$ cysteine and the $23^{rd}$ cysteine are bonded by a disulfide bond to form a ring structure. ANP has been shown to have diuretic effects in the kidneys and relaxes/dilates vascular smooth muscle cells in the blood vessels. In contrast, human BNP is a peptide produced and released by ventricular cells, and is composed of 32 amino acids, of which the $10^{th}$ cysteine and the $26^{th}$ cysteine are bonded by a disulfide bond to form a ring structure. BNP also possesses both diuretic and vasodilating effects. BNP was originally isolated and identified in the porcine brain in Japan in 1988, and is also called brain natriuretic peptide.

Both ANP and BNP bind to the receptor NPR-A (also called GC-A) having a guanylate cyclase domain, and exert their effects as stated above by stimulating the production of cGMP. In fact, secretion of ANP is stimulated in response to an increase in the atrial pressure by its distension in congestive heart failure, etc., and through its action as stated above, ANP relieves the symptoms of congestive heart failure, etc. Likewise, BNP's release is stimulated during certain conditions including myocardial infarction, and BNP, through its action as described above, relieves the symptoms associated with myocardial infarction, etc. (Refer to non-patent literature 1). Although most of the circulating BNP derives from the ventricles, some BNP is released by the atria. In cardiac failure, the level of expression of both ANP and BNP increases to as much as 100 times more the normal level, but the increase of BNP expression is reported to be both greater and faster than that of ANP. While ANP (hANP) is marketed as a prescription drug for treating acute cardiac failure in Japan, BNP is clinically used in the United States.

(2) CNP:

CNP, which was once thought to function only as a brain peptide because it was first found in the brain, has now been clarified to exist in the periphery as well. In the vascular walls, in particular, CNP specific receptors were found to be abundant in the smooth muscle cells, and CNP to be produced by the cells of the monocyte/macrophage linage and the endothelial cells. For those reasons, CNP is speculated to function in the vascular walls as a local mediator involved in inhibition of growth of vascular smooth muscle cells. Its clinical application is currently being investigated for possible prevention of restenosis by CNP administration, which occurs with a certain frequency after percutaneous transluminal coronary angioplasty (PTCA) performed on patients with ischemic heart failure.

Recently it has been reported that intravenous administration of CNP remarkably improves cardiomegaly and fibrosis associated with myocardial infarction, and improves cardiac functions in animal experiments. Cardiac fibrosis is known to cause diastolic ventricular failure and cardiac dysrhythmia. Since CNP possesses a powerful action to suppress fibroblast proliferation, the potential of CNP as an anti-fibrotic medication for the heart is under investigation. Since CNP is a hormone occurring naturally in the body, there is little concern of adverse side effects; accordingly clinical application of CNP as a therapeutic preparation for arteriosclerotic diseases and heart diseases is expected. Here, examples of CNP include CNP-22 composed of 22 amino acids, and CNP-53 wherein 31 amino acid residues are attached to the N-terminal of CNP-22.

(3) Natriuretic Peptide Receptors:

Natriuretic peptide receptors are classified into three subtypes; NPR-A receptor (also called GC-A) and NPR-B receptor (also called GC-B) both of which contain a guanylate cyclase domain, and NPR-C receptor which lacks a guanylate cyclase domain. It is known that ANP can bind to NPR-A and NPR-C receptors, BNP can bind to NPR-A and NPR-C receptors, and CNP can bind to NPR-B and NPR-C receptors.

The activation of NPR-A receptors is suggested to induce vasodilation, a diuretic effect, and inhibition of cell growth, while NPR-B receptors are abundant in vascular smooth muscle cells and thought to be involved in the growth inhibition of vascular smooth muscle cells.

(4) Relationship Between Natriuretic Peptides and the Immune System:

Historically, natriuretic peptides were first discovered as a peptide released from the atria, later named ANP, and its vasodilating and diuretic actions gathered attention. BNP and CNP were then discovered as peptides similar to ANP. This historical background offers an explanation as to why any attention to the relationship between natriuretic peptides and the immune system have been focused on those related to the cardiovascular system. CNP knock-out mice demonstrated impaired growth of cartilage resulting in a dwarfism-like phenotype (refer to Non-patent literature 2), which directed some interest to the relationship between arthritis and natriuretic peptides.

ANP is implicated in playing a role in arthritis and sepsis as it inhibits the release of inflammatory cytokines including tumor necrosis factor (TNF-$\alpha$) and interleukin 1$\beta$ (IL-1$\beta$) by macrophages (refer to Non-patent literature 3). This literature, however, does not mention ANP's relationship with rhinitis.

Similarly, the blood concentration of BNP has been reported to increase with the rejection response following heart transplant, and therefore it is suggested that it is associated with immune regulation in the cardiovascular system (refer to Non-patent literature 4). However, this literature does not describe any connection between BNP and rhinitis.

Taking into account the observation that there is an increase in the blood concentration of BNP during the heart graft rejection, Kuroski de Bold et al. have investigated the immunoregulatory action of natriuretic peptides, and have demonstrated that both ANP and BNP inhibit the lymphocyte growth (refer to Non-patent literature 5). However, there is no connection between natriuretic peptides and rhinitis mentioned in this literature.

Chiurchiu et al. on the other hand have investigated the immunoregulatory actions of BNP focusing on its association with heart disease and sepsis, and showed that BNP promotes the release by macrophages of pro-inflammatory cytokines such as arachidonic acid, prostaglandin E2 (PGE2), and leukotriene B4 (LTB4), and also promotes the release of anti-inflammatory cytokines including interleukin 10 (IL10). Thus, while BNP is indicated to have some action in the regulation of inflammatory responses, whether BNP acts overall to suppress or promote inflammatory responses remains inconclusive in the literature (refer to Non-patent literature 6). This literature also does not mention any connection between BNP and rhinitis.

Similarly, CNP is reported to be released by macrophages (refer to Non-patent literature 7), and while investigating the roles of CNP in cardiac ischemia and myocardial damage after reperfusion, Scotland et al. report that CNP suppresses platelet aggregation and lymphocyte migration (refer to Non-patent literature 8). The connection between CNP and rhinitis, however, is not described in these literatures.

Likewise, Obata et al. examined the roles played by CNP in myocarditis using a rat myocarditis model generated by injecting pig myosin. They reported that continuous administration of CNP for 1 week to the model suppressed necrosis and inflammation of the cardiac tissues, while at the same time promoted the regeneration of blood vessels, thereby preventing functional loss of the heart (refer to Non-patent literature 9). Nevertheless, there is no mention in this literature to suggest a connection between CNP and rhinitis.

In addition, based on the observation that CNP knock-out mice show a dwarfism-like phenotype, attention has been paid to the potential connection between CNP and cartilage growth. Agoston et al. demonstrated that when incubated with Dexamethasone, the primary-cultured chondrocytes extracted from the tibial bones of mouse embryos had significantly increased the expression of CNP genes (refer to Non-patent literature 10). This literature, however does not describe any connections between CNP and rhinitis.

It is evident that the connections between natriuretic peptides and the immune system have drawn increasing attention in recently years, but it is limited only to the inflammation of the cardiovascular system and arthritis, and the relationship between rhinitis and natriuretic peptides have never been reported.

(5) Reports on the Application of Natriuretic Peptides:

Following are some examples of a number of applications of CNP, BNP and ANP.

Toshiko Koide and her colleagues have proposed a preparation for repair/regeneration of tissues and organs, comprising a composition that comprises any of ANP, BNP, CNP, urodilatin (P-Uro), precursors thereof, derivatives thereof, or combinations thereof as an active ingredient, and that may comprise pharmaceutically commonly-used diluents, excipients, fillers, and auxiliary agents (refer to Patent Literature 1).

However, specific examples of repair and regeneration of tissues and organs relate only to the regeneration of myocardiocytes, hypodermal tissue, hair, and improvement of cracked, rough skin due to wet works; they all correspond to ANP administration. There is no statement that implies therapeutic preparations for treating rhinitis by means of administration of CNP or BNP.

Masaharu Tanaka and his colleagues have proposed a C-type natriuretic peptide exhibiting a growth inhibitory action of vascular smooth muscle cells, as well as a growth inhibitory preparation of vascular smooth muscle cells containing such peptide as its active ingredient (refer to Patent Literature 2).

This, however, relates to the use of CNP in a growth inhibitory agent of vascular smooth muscle cells but does not imply application of CNP or BNP to therapeutic preparations for rhinitis.

Katsuhiko Nakada and his colleagues proposed an eye drop for promoting lacrimal secretion or for treating keratoconjunctival disorder, containing as its active ingredient a natriuretic peptide, and they listed ANP, BNP and CNP as examples of usable natriuretic peptides (refer to Patent Literature 3).

This, however, only relates to the application of the property of ANP, CNP and BNP to promote lacrimal secretion in an eye drop for treating keratoconjunctival disorder, and does not indicate the use of CNP or BNP in a therapeutic preparation to treat rhinitis.

Kazuwa Nakao and his colleagues proposed a composition for increasing the body height containing a guanyl cyclase B (GC-B) activator as the active ingredient, which is to be administered to an individual without FGFR3 abnormality (refer to Patent Literature 4).

This indicates an application of CNP in a composition for increasing the body height based on the finding that the nose-anus length in the transgenic mice overexpressing CNP was larger than that in normal litters, but does not imply the use of CNP or BNP in a therapeutic preparation for rhinitis.

Kazuwa Nakao and his colleagues also proposed a prophylactic agent or therapeutic preparation for the inflammation of the joints containing a guanyl cyclase B (GC-B) activator such as CNP as an active ingredient (refer to Patent Literature 5).

However, this relates only to the application of CNP in a therapeutic preparation or prophylactic preparation for inflammation of the joints based on the study revealing that, compared to their litter mates, the articular cartilages grow thicker in the transgenic mice overexpressing CNP, along with the observation that the arthritis is repressed by the continuous administration of CNP to model animals of arthritis. Hence this does not imply the application of CNP or BNP in a therapeutic preparation for rhinitis.

In addition, Masaharu Tanaka and his colleagues reported that CNP differs from ANP and BNP in the structure, function and effects as stated below (refer to Patent Literature 2).

"At present, both ANP and BNP are thought to act as a hormone secreted by the heart into the blood, as well as a neurotransmitter, and to play an important role in maintaining the amount of body fluid and homeostasis of blood pressure . . . . There are many unknown points in the physiological role of CNP as a natriuretic peptide. Namely, since CNP has a primary amino acid sequence similar to that of ANP and BNP and shows a natriuretic action and a hypotensive action upon in vitro administration, CNP was relegated to the natriuretic peptide family. However, because the natriuretic action and hypotensive action of CNP are significantly weaker than those of ANP and BNP (from $\frac{1}{50}$ to $\frac{1}{100}$), . . . CNP has held a unique position in the natriuretic peptide family, and has been presumed to be playing a role different from the maintenance of amounts of body fluid and homeostasis of blood pressure . . . . Comparing the structure of CNP with that of ANP/BNP, CNP differs from ANP or BNP in the following points . . . . Namely, the primary amino acid sequence of CNP completely differs from that of ANP or BNP at the exocyclic N-terminal domain; of the 17 amino acid residues in the endocyclic domain, 5 residues and 4 residues in CNP differ from those in ANP and BNP, respectively. In addition, the structure of the exocyclic C-terminal domain of CNP largely differs from that of ANP or BNP, and CNP does not have a tail structure existing in ANP or BNP (in the case of ANP and BNP, 5 amino acid residues and 6 amino acid resides, respectively, are attached to the C-terminal of the cyclic structure in ANP and BNP; this structure is called a tail structure for descriptive purposes). Thus-described structural differences between CNP and ANP/BNP are clearly involved in the manifestation of the above-mentioned characteristic pharmacological effects of CNP."

REFERENCE LIST

Patent Literature

Patent Literature 1: JP A 2008-162987
Patent Literature 2: JP A 6-9688
Patent Literature 3: JP A 2000-169387
Patent Literature 4: WO 2005/094890
Patent Literature 5: WO 2005/094889

Non-Patent Literature

Non-patent Literature 1: European J. Endocrinology, Vol. 135, p. 265, 1996.
Non-patent Literature 2: Proceedings of the National Academy of Sciences of the United States of America, Vol. 98, No. 7, p. 4016, 2001.
Non-patent Literature 3: Annals of the Rheumatic Disease, Vol. 60, Suppl. 3, iii, p. 68, 2001.
Non-patent Literature 4: The Journal of Heart and Lung Transplantation, Vol. 27, p. 31, 2008.
Non-patent Literature 5: The Journal of Heart and Lung Transplantation, Vol. 29, No. 3, p. 323, 2010.
Non-patent Literature 6: Regulatory Peptides, Vol. 148, p. 26, 2008.
Non-patent Literature 7: Experimental Hematology, Vol. 29, p. 609, 2001.
Non-patent Literature 8: Proceedings of the National Academy of Sciences, Vol. 102, No. 40, p. 14452, 2005.

Non-patent Literature 9: Biochemical and Biophysical Research Communications, Vol. 356, p. 60, 2007.
Non-patent Literature 10: BMC Musculoskeletal Disorders, Vol. 7, p. 87, 2006.

SUMMARY OF INVENTION

Problem to be Solved by Invention

Rhinitis, in particular allergic rhinitis, is a recurrent disease therefore its treatment requires continuous use of drugs. However, as mentioned above, while a steroid nasal spray has strong local effects even in small amounts, occasionally it also induces local side effects such as nasal irritation, dryness, nose burning sensation, and nasal bleeding, and it inevitably involves complications of infection and others due to long-term use. Antihistamine drugs suppress allergic reactions and their symptoms, but they have disadvantages such as drying of the nasal mucous membrane and inducing drowsiness.

Accordingly, the object of the present invention is to provide a novel therapeutic preparation for rhinitis that is not only efficacious and safe for patients with rhinitis, in particular patients with allergic rhinitis, but also has no side effects such as nasal irritation, dryness, nose burning sensation, nasal bleeding, and drowsiness, etc.

Means of Solving the Problem

Considering these conditions, as a result of strenuous research efforts, the present inventor have found that C-type natriuretic peptide (CNP) and B-type natriuretic peptide (BNP), conventionally known as a suppressant of vascular smooth muscle cell proliferation, have excellent efficacy and safety as a therapeutic preparation for rhinitis, in particular allergic rhinitis, and also confirmed that they can be applied to patients with a sensitive mucous membrane without causing irritation symptoms; the present invention has thus been accomplished.

The present invention specifically includes the following.

[1] A therapeutic preparation for rhinitis comprising C-type natriuretic peptide (CNP) or B-type natriuretic peptide (BNP) as the active ingredient.

[2] The therapeutic preparation for rhinitis according to [1], wherein the C-type natriuretic peptide (CNP) is CNP-22, CNP-53, or a CNP derivative in which any amino acid in the amino acid sequence of CNP-22 or CNP-53 is deleted, substituted or added, and which has CNP activity.

[3] The therapeutic preparation for rhinitis according to [1], wherein the C-type natriuretic peptide (CNP) is CNP-22.

[4] The therapeutic preparation for rhinitis according to [1], wherein the B-type natriuretic peptide (BNP) is BNP-26, BNP-32, BNP-45, or a BNP derivative in which any amino acid in the amino acid sequence of BNP-26, BNP-32, or BNP-45 is deleted, substituted or added, and which has BNP activity.

[5] The therapeutic preparation for rhinitis according to [1], wherein the B-type natriuretic peptide (BNP) is BNP-32.

[6] The therapeutic preparation for rhinitis according to [1], wherein the C-type natriuretic peptide (CNP) or B-type natriuretic peptide (BNP) is a chimeric peptide of CNP and BNP forming a ring structure by an intermolecular disulfide bond, in which the CNP is a peptide selected from the group consisting of CNP-22, CNP-53, a peptide comprising any amino acid sequence of 5 or more consecutive amino acids in the amino acid sequence of CNP-22 having deletion(s), substitution(s), or addition(s) of any 1-5 amino acid(s), or a peptide comprising any amino acid sequence of 5 or more consecutive amino acids in the amino acid sequence of CNP-53 having deletion(s), substitution(s), or addition(s) of any 1-5 amino acid(s), and in which the BNP is a peptide selected from the group consisting of BNP-26, BNP-32, BNP-45, a peptide comprising any amino acid sequence of 5 or more consecutive amino acids in the amino acid sequence of BNP-26 having deletion(s), substitution(s), or addition(s) of any 1-5 amino acid(s), a peptide comprising any amino acid sequence of 5 or more consecutive amino acids in the amino acid sequence of BNP-32 having deletion(s), substitution(s), or addition(s) of any 1-5 amino acid(s), or a peptide comprising any amino acid sequence of 5 or more consecutive amino acids in the amino acid sequence of BNP-45 having deletion(s), substitution(s), or addition(s) of any 1-5 amino acid(s), and wherein the chimeric peptide has CNP activity or BNP activity; or a derivative of the chimeric peptide.

[7] The therapeutic preparation for rhinitis according to [1], wherein the concentration of the C-type natriuretic peptide (CNP) or the B-type natriuretic peptide (BNP) is 20-200 µg/g.

[8] The therapeutic preparation for rhinitis according to [1], wherein the concentration of the C-type natriuretic peptide (CNP) or the B-type natriuretic peptide (BNP) is 50-200 µg/g.

[9] The therapeutic preparation for rhinitis according to [1], wherein the concentration of the C-type natriuretic peptide (CNP) or the B-type natriuretic peptide (BNP) is 50-100 µg/g.

[10] The therapeutic preparation for rhinitis according to [1], wherein the rhinitis is infectious rhinitis, hypersensitive non-infectious rhinitis, irritant rhinitis, atrophic rhinitis, or specific granulomatous rhinitis.

[11] The therapeutic preparation for rhinitis according to [10], wherein the infectious rhinitis is acute rhinitis or chronic rhinitis.

[12] The therapeutic preparation for rhinitis according to [10], wherein the hypersensitive non-infectious rhinitis is combined-type rhinitis (hypersensitive nose), rhinorrhea-type rhinitis, congestive-type rhinitis, or dry-type rhinitis.

[13] The therapeutic preparation for rhinitis according to [12], wherein the combined-type rhinitis (hypersensitive nose) is allergic rhinitis.

[14] The therapeutic preparation for rhinitis according to [1], wherein the allergic rhinitis is allergic rhinitis against at least one allergen selected from the group consisting of house dust, mite, cedar, orchard grass, ragweed, and cat hair.

[15] The therapeutic preparation for rhinitis according to [10], wherein the irritant rhinitis is physical irritant-induced rhinitis, chemical irritant-induced rhinitis or radiation-induced rhinitis.

[16] The therapeutic preparation for rhinitis according to [1], wherein the rhinitis is atrophic rhinitis or specific granulomatous rhinitis.

[17] The therapeutic preparation for rhinitis according to [1], wherein the rhinitis is mixed-type rhinitis, sneezing/rhinorrhea-type rhinitis, or nasal-occlusion-type rhinitis.

[18] The therapeutic preparation for rhinitis according to [1], wherein the dosage form is a nasal drop preparation selected from an ointment preparation, a gel preparation, a cream preparation, a lotion preparation, a liquid preparation, a powder preparation or a spray preparation.

[19] The therapeutic preparation for rhinitis according to [1], wherein the dosage form is a nasal drop preparation selected from a gel preparation, a liquid preparation or a spray preparation.
[20] The therapeutic preparation for rhinitis according to [1], wherein the rhinitis is rhinitis in a subject suffering from atopic dermatitis.
[21] The therapeutic preparation for rhinitis according to [1], wherein the rhinitis is rhinitis with treatment resistance to steroids.
[22] The therapeutic preparation for rhinitis according to [1], wherein the rhinitis is rhinitis in a subject having difficulty with withdrawal from steroids.
[23] The therapeutic preparation for rhinitis according to [1], wherein the rhinitis is rhinitis with treatment resistance to antihistamine drugs.

Advantageous Effects of Invention

The therapeutic preparation for rhinitis of the present invention has, as is clear from the case studies mentioned below, not only excellent actions to improve rhinorrhea and nasal occlusion and to eliminate sneezing and nasal itching, but also superior permeability (absorbability) to the nasal mucous membrane and persistence. It is fast-acting and causes no irritation to patients with sensitive nasal mucous membranes, no local side effects as well as no systemic side effects such as induction of drowsiness.

The therapeutic preparation for rhinitis of the present invention has CNP or BNP as the active ingredient, and its effects are more remarkable compared to conventional steroids and antihistamine drugs. In terms of persistence of the effects, it is a revolutionary preparation that can relieve symptoms by once-a-day administration.

Thus, without administration of steroids or antihistamine drugs, severe symptoms of rhinitis can be markedly improved by the use of the therapeutic preparation for rhinitis of the present invention once a day, and even after discontinuation or stoppage of the use, worsening of symptoms need not be a concern.

Moreover, since the therapeutic preparation for rhinitis of the present invention has long-lasting drug efficacy, while at first, use twice a day in the morning and before bedtime is recommended, in many cases application once a day from day 2 and thereafter can significantly improve symptoms such as sneezing, rhinorrhea, and nasal occlusion.

Regarding the absorbability and fast-acting property, the effects are manifested 10 to 20 min after the inhalation, and the preparation of the present invention is effective for any of mixed-type rhinitis, nasal-occlusion-type rhinitis, and sneezing/rhinorrhea-type rhinitis. Therapeutic effects in actual case studies (16 cases) showed that the preparation of the present invention was effective in 100% of the cases.

Given that both BNP and ANP belong to the same family and share the common receptors, it was formerly assumed that BNP and ANP preparations possess equivalent effects. When they were actually tested on patients with rhinitis, allergic rhinitis in particular, however, BNP preparations were revealed to have much greater pharmacological effects than ANP preparations. That is to say that BNP preparations are faster-acting than ANP preparations, and lead to better improvements of the clinical symptoms and the effects lasted longer. On the other hand, ANP preparations unexpectedly resulted in much poorer improvements in the rhinitis symptoms including runny nose, rhinorrhea and nasal occlusion, and in many cases, the symptoms showed no improvements or worsening. In cases where little improvement was evident with ANP preparations, the improvement in the rhinitis symptoms was insufficient and only temporary. The finding that BNP as a therapeutic preparation for rhinitis had more intense pharmacological effects than ANP belonging to the same family of natriuretic peptide was surprising.

The active ingredients of the present invention, CNP and BNP, are hormones which naturally occur in the body. Thus side effects are less expected and with adequate dosage, it is thought to have only a minor effect on the hemodynamic status and hence it is safe to apply to patients with low or unstable blood pressure, allowing long-term administration to chronic rhinitis patients. It shows a potency to rhinitis greater than that of conventional steroids and antihistamine drugs and it is also more rapid-acting, with an enhanced efficacy and leads to longer-lasting effects; in many cases, application of once a day from day 2 and thereafter can significantly improve symptoms such as sneezing, rhinorrhea, and nasal occlusion. By the use of CNP preparations or BNP preparations, in most cases, a mild to below mild and stable condition can be maintained without combined internal use of antihistamine agents, and it is also advantageous that there are no local irritation symptoms that are observed with steroid sprays. In addition, the therapeutic preparation for rhinitis of the present invention has a merit of being efficacious to patients who are resistant to steroid therapy or patients of severe cases, which makes the present invention an unprecedented, important therapeutic preparation.

Thus, the therapeutic preparation for rhinitis of the present invention is extremely effective in the treatment of various types of rhinitis, in particular allergic rhinitis, and side effects need not be a concern; the present preparation can be applied to patients in whom conventional steroid nasal sprays and antihistamine drugs are not effective, or patients in whom these drugs cannot be applied due to the possibility of side effects, as well as young patients.

Therefore, practical application of the therapeutic preparation for rhinitis of the present invention as a therapeutic preparation for rhinitis replacing steroids and antihistamine drugs can be greatly expected.

BRIEF DESCRIPTION OF DRAWINGS

FIG. 1 is a diagram showing a comparison of the amino acid sequences of human CNP peptide, human BNP peptide, and human ANP peptide. Each letter of the alphabet represents a type of amino acid expressed by one letter. There are three common regions in the amino acid sequence among the human CNP peptide, human BNP peptide and human ANP peptide, i.e., amino acid sequences represented by "CFG", "DRI" and "SGLGC" (SEQ ID NO:21); each peptide has four mutually different sequences divided by these three common sequences.

FIG. 2 is a graph showing the therapeutic effects on rhinitis before and after spraying CNP nasal drop preparations. Each point represents each case. In all of nine (9) severe cases and one (1) moderate case, symptoms were improved to a mild degree by the 100 µg/ml CNP nasal drop preparation.

FIG. 3 is a graph showing the therapeutic effects on rhinitis before and after spraying BNP nasal drop preparations. Each point represents each case. In two (2) most severe cases and one (1) moderate case, symptoms were improved to a mild degree by spraying the 50 µg/ml BNP nasal drop preparation. In addition, in one most severe case, symptoms were improved to a moderate degree by spraying the 50 µg/ml BNP nasal drop preparation. Similarly, in one (1) most severe case, symptoms were improved to a mild degree by spraying the 100 μg/ml BNP nasal drop preparation. Similarly, in one (1) severe case, symptoms were improved to a mild degree by spraying the 200 μg/ml BNP nasal drop preparation.

EMBODIMENTS FOR CARRYING OUT THE INVENTION

The present invention relates to a therapeutic preparation for rhinitis comprising C-type natriuretic peptide (CNP) or B-type natriuretic peptide (BNP) as the active ingredient.

The CNP referred to herein means: CNP-22 composed of 22 amino acids, and CNP-53 in which 31 amino acid residues are attached to the N-terminal of the CNP-22, or derivatives thereof, without any particular limitations provided that they possess CNP activity. These CNP-22, CNP-53, and their derivatives are all heretofore known, and can be made by chemical synthesis or genetic manipulations.

There are no particular limitations to the origin of CNP-22 and CNP-53, on the condition that they possess CNP activity, but the CNP derived from mammals including human or birds are preferred, and more preferably, the CNP derived from humans, monkeys, mice, rats or pigs, and particularly preferably, the CNP derived from humans.

The CNP derivatives means those having, in the amino acid sequences of the CNP-22 or CNP-53, a deletion(s), substitution(s) or addition(s) of 1-5 amino acid(s), more preferably 1-3 amino acid(s), and furthermore preferably 1 or 2 amino acid(s), while possessing CNP activity, or alternatively, those having a sequence with a homology of 85% or more, preferably 90% or more, and more preferably 95% or more with the amino acid sequence of the CNP-22 or CNP-53, while possessing CNP activity.

Replaceable amino acids are substituted ideally by conservative amino acid substitution. Conservative amino acids are classified by polarities and charge types. For example, nonpolar uncharged amino acids include glycine, alanine, valine, leucine, isoleucine, proline, etc.; aromatic aminoacids include phenylalanine, tyrosine, tryptophan; polar uncharged amino acids include serine, threonine, cysteine, methionine, asparagine, glutamine, etc.; negatively-charged amino acids include asparaginic acid, glutamic acid; positively-charged amino acids include lysine, arginine, histidine. Thus, preferably amino-acid substitution is carried out between conservative amino acids belonging to the same group. Here, when proline is to be replaced by another nonpolar uncharged amino acid, or when proline is to replace other nonpolar uncharged amino acids, it should be noted that proline is not flexible in its spatial orientation. Similarly, when cysteine is to be replaced by another polar uncharged amino acid, or when cysteine is to replace other polar uncharged amino acids, it should be noted that cysteine may form a disulfide bond with another cysteine.

CNP derivatives may include those amidated or methoxylated at the C terminal, CNP modified with addition of polyethylene glycol or fatty acids, and, glycosylated or alkylated CNP, provided they have CNP activity.

Thus, any heretofore known CNPs with CNP activity can be used in the present invention. Examples may include CNP derivatives disclosed in JP A 6-9688, CNP derivatives disclosed in U.S. Pat. No. 5,583,108, and CD-NP disclosed in U.S. Pat. No. 6,818,619. It is possible to test the presence/absence of CNP activity easily using heretofore known procedures, such as by testing a growth inhibitory action on the vascular smooth muscle cells, or by examining the activity of cGMP production in the cells expressing NPR-B receptors.

While any of CNP-22, CNP-53 and their derivatives can be used as the active ingredient of the present invention, CNP-22 with a lower molecular weight is more preferable in terms of absorbability. CNP-22 can be manufactured by chemical synthesis or genetic manipulation using human CNP genes, and is also available at, for example, Peptide Institute Inc. as CNP-22 (human).

CNP that can be used in the present invention includes: purified naturally occurring CNP, genetically engineered CNP made using known genetic engineering procedures, CNP made using known chemical synthetic procedures (such as solid-phase peptide synthesis by peptide synthetic machinery). Basic methods including genetic engineering techniques, site-specific mutagenesis, and PCR, are commonly known or heretofore known, and are described in, for example, Current Protocols In Molecular Biology; John Wiley & Sons (1998), and JP A 5-207891.

The BNP of the present invention refers to: BNP-26 containing 26 amino acids, BNP-32 containing 32 amino acids, BNP-45 containing 45 amino acids, or their derivatives without any particular limitations provided they possess BNP activity. BNP can also be high molecular weight γ-BNP (molecular weight of approximately 13000) which is formed by the removal of the signal peptide from a BNP precursor. BNP-32 and their derivatives are preferred. BNP-26, BNP-32, BNP-45, and their derivatives are heretofore known, and can be manufactured by chemical synthesis or genetic manipulation.

There are no particular limitations to the origin of the BNP-26, BNP-32 and BNP-45, provided they possess BNP activity, but the CNP derived from mammals including humans or birds is preferred, and the CNP derived from humans, monkeys, mice, rats or pigs is more preferred, and the CNP derived from humans is particularly preferred.

The BNP derivatives means, those having, in the amino acid sequences of BNP-26, BNP-32 or BNP-45, a deletion(s), addition(s) or substitution(s) of 1-5 amino acid(s), more preferably 1-3 amino acid(s), and furthermore preferably 1 or 2 amino acid(s), while possessing BNP activity, or alternatively, those having a sequence with a homology of 85% or more, preferably 90% or more, and more preferably 95% or more with the amino acid sequence of BNP-26, BNP-32 or BNP-45, while possessing BNP activity.

Replaceable amino acids in the BNP derivatives are similar to the replaceable amino acids in the CNP derivatives.

BNP derivatives may include those amidated or methoxylated at the C terminal of BNP, BNP modified with addition of polyethylene glycol or fatty acids, and, glycosylated or alkylated BNP, provided they have BNP activity.

Thus, any heretofore known BNP with BNP activity can be used in the present invention. Examples may include BNP derivatives disclosed in JP A 2007-525213, BNP derivatives disclosed in U.S. Pat. No. 6,028,055, BNP derivatives disclosed in U.S. Pat. No. 5,114,923, and BD-NP disclosed in U.S. Pat. No. 6,818,619, or diuretic polypeptide or natriuretic polypeptide disclosed in JP A 2010-500032.

It is possible to easily test the presence/absence of BNP activity using heretofore known procedures, such as an examination of the activity of cGMP production in the cells expressing NPR-A receptors.

While any of BNP-26, BNP-32, BNP-45 and their derivatives can be used as the active ingredient of the present invention, BNP-32 is preferable in terms of drug efficacy and availability.

BNP of the present invention can be manufactured by chemical synthesis or genetic manipulation using human BNP genes (for example, refer to JP A5-207891, JP A2007-525957, JP A2007-525213), and BNP is also commercially available since it has already been launched. Alternatively, it is available from, for example, Peptide Institute Inc. as BNP-32 (human).

BNP that can be used in the present invention includes: purified naturally occurring BNP, genetically engineered BNP made using known genetic engineering procedures, BNP made using known chemical synthetic procedures (such as solid-phase peptide synthesis by a peptide synthesizer). Basic methods including genetic engineering techniques, site-specific mutagenesis, and PCR, are commonly known or heretofore known, and are described in, for example, Current Protocols in Molecular Biology; John Wiley & Sons (1998), and JP A 5-207891.

When the term "CNP or BNP" is used herein, it refers to either CNP or BNP, as well as the chimeric peptides of CNP and BNP. That is, as used herein, the term "CNP or BNP" refers to CNP or BNP which may be: a chimeric peptide of CNP and BNP forming a ring structure by an intermolecular disulfide bond, in which the CNP is a peptide selected from the group consisting of CNP-22, CNP-53, a peptide comprising any amino acid sequence of 5 or more consecutive amino acids in the amino acid sequence of CNP-22 having deletion(s), substitution(s), or addition(s) of any 1-5 amino acid(s), or a peptide comprising any amino acid sequence of 5 or more consecutive amino acids in the amino acid sequence of CNP-53 having deletion(s), substitution(s), or addition(s) of any 1-5 amino acid(s),
and in which the BNP is a peptide selected from the group consisting of BNP-26, BNP-32, BNP-45, a peptide comprising any amino acid sequence of 5 or more consecutive amino acids in the amino acid sequence of BNP-26 having deletion(s), substitution(s), or addition(s) of any 1-5 amino acid(s), a peptide comprising any amino acid sequence of 5 or more consecutive amino acids in the amino acid sequence of BNP-32 having deletion(s), substitution(s), or addition(s) of any 1-5 amino acid (s), or a peptide comprising any amino acid sequence of 5 or more consecutive amino acids in the amino acid sequence of BNP-45 having deletion(s), substitution(s), or addition(s) of any 1-5 amino acid(s), and wherein the chimeric peptide has CNP activity or BNP activity; or a derivative of the chimeric peptide.

Here, there are no particular limitations to the origin of CNP-22 and CNP-53, provided that they possess CNP activity, but the CNP derived from mammals including humans or birds are preferred, and more preferably, CNP derived from humans, monkeys, mice, rats or pigs, and most preferably, CNP derived from humans. Similarly, there are no particular limitations to the origin of BNP-26, BNP-32 and BNP-45, provided that they possess BNP activity, but the BNP derived from mammals including humans or birds is preferred, and the BNP derived from humans, monkeys, mice, rats or pigs is more preferred, and the BNP derived from humans is particularly preferred.

The derivatives of chimeric peptide of CNP and BNP mean those which have, in the amino acid sequences of the chimeric peptide of CNP and BNP, deletion(s), addition(s) or substitution(s) of preferably 1-5 amino acid(s), more preferably 1-3 amino acid(s), and further more preferably 1 or 2 amino acid(s), while possessing CNP or BNP activity.

Replaceable amino acids in the derivatives of the chimeric peptide of CNP and BNP are similar to the replaceable amino acids in the CNP derivatives.

The derivatives of chimeric peptide of CNP and BNP may include those amidated or methoxylated at a C terminal of the chimeric peptide of CNP and BNP, those modified with the addition of polyethylene glycol or fatty acids in the chimeric peptide of CNP and BNP, and, glycosylated or alkylated chimeric peptide of CNP and BNP, provided that they have CNP or BNP activity.

Furthermore, the amino acid sequence of human CNP peptide represented by SEQ ID NO: 1 and the amino acid sequence of human BNP peptide represented by SEQ ID NO: 2 have, as shown in FIG. 1, four mutually different sequences divided by three common sequences represented by the amino acid sequences of "CFG", "DRI" and "SGLGC" (SEQ ID NO:21). Accordingly, as a chimeric peptide of CNP and BNP, at least 14 kinds of chimeric peptide represented by SEQ ID NOs 3-16 are listed based on the combination of these four mutually different sequences. Then, these chimeric peptides and their derivatives are considered to have characteristics common to CNP and BNP. Namely, these chimeric peptides and their derivatives can be used as the active ingredient of the therapeutic preparation for rhinitis of the present invention.

Thus, it is possible to use any heretofore known chimeric peptides of CNP and BNP or derivatives thereof in the present invention, provided that they possess CNP or BNP activity. For example, aquaretic polypeptides and natriuretic polypeptides disclosed as ABC-NP, ABC-NP1, BC-NP, etc. in JP A 2010-502231 may be used. These polypeptides are exemplified as amino acid sequence of SEQ ID Nos. 17-20.

The presence/absence of CNP or BNP activity can be easily tested using heretofore known procedures, such as an examination of the activity of cGMP production in the cells expressing NPR-A receptors or in the cells expressing NPR-B.

The chimeric peptides of CNP and BNP and their derivatives of the present invention can also be manufactured by chemical synthesis or by genetic manipulation.

Indications of treatment by the therapeutic preparation for rhinitis of the present invention are not particularly limited, as long as the disease is a so-called rhinitis, which induces an inflammation of the nasal mucous membrane and shows symptoms such as sneezing, runny nose and stuffy nose. The therapeutic preparation for rhinitis of the present invention may be applied to various types of rhinitis.

More specifically, rhinitides to which the therapeutic preparation for rhinitis of the present invention can be applied include infectious rhinitis, hypersensitive non-infectious rhinitis, irritant rhinitis, atrophic rhinitis or specific granulomatous rhinitis; preferably it is infectious rhinitis and hypersensitive non-infectious rhinitis in terms of therapeutic effects, and particularly preferably it is hypersensitive non-infectious rhinitis.

Infectious rhinitis may be acute rhinitis or chronic rhinitis, and preferably acute rhinitis. Using the therapeutic preparation for rhinitis of the invention, sneezing, excess rhinorrhea (nasal drip), nasal occlusion (stuffy nose), and impairment of the sense of smell, etc. can be rapidly cured.

Hypersensitive non-infectious rhinitis may be combined-type rhinitis (hypersensitive nose) including allergic rhinitis and non-allergic rhinitis; rhinorrhea-type rhinitis selected from gustatory rhinitis, cold air inhalation-induced rhinitis, and senile rhinitis; congestive-type rhinitis selected from drug-induced rhinitis, psychogenic rhinitis, pregnancy rhinitis, endocrine rhinitis and cold-induced rhinitis; or dry-type rhinitis.

Particularly preferred is allergic rhinitis or non-allergic rhinitis, and allergic rhinitis may include both perennial allergic rhinitis and seasonal allergic rhinitis. The therapeutic preparation for rhinitis of the invention exhibits extremely high efficacy and safety for allergic rhinitis, in particular perennial allergic rhinitis caused by house dust or mites, of which complete cure or long-term remission is considered to be difficult, as its effective therapeutic preparation.

In addition, the present preparation is efficacious as a therapeutic preparation for various types of rhinitis with symptoms such as sneezing, runny nose and stuffy nose, derived from irritant rhinitis such as physical irritant-induced rhinitis, chemical irritant-induced rhinitis and radiation-induced rhinitis, as well as atrophic rhinitis and specific granulomatous rhinitis.

Furthermore, when indication of treatment by the present therapeutic preparation for rhinitis is classified based on the symptoms, the preparation can be effectively used for mixed-type rhinitis, nasal-occlusion-type rhinitis, or sneezing/rhinorrhea-type rhinitis in accordance with "Guidelines for medical care of nasal allergies, 2009 edition" (edited by the committee for creation of guidelines for medical care of nasal allergies).

Meanwhile, the meaning of the terms and the characteristics of the symptoms of these various types of rhinitis are as descried above in the Background Art.

The therapeutic preparation for rhinitis of the present invention is those comprising C-type natriuretic peptide (CNP) or B-type natriuretic peptide (BNP) as the active ingredient, and its administration route and dosage form are not particularly limited.

Regarding the administration route, injections, oral medicines or external preparations can be used depending on the patient and symptoms. Specific examples include nasal drop preparations, gel preparations, ointment preparations, cream preparations, lotion preparations, spray preparations, liquid preparations, nasal spray preparations, patch preparations, aerosol preparations, jelly preparations, cataplasms, patch preparations, plaster preparations, suspension preparations, emulsion preparations, injection preparations, tablets, pills, capsules, granules, powders, etc.; liquid preparations may be adopted by selecting appropriate solvents. Any preparation can be produced in accordance with well-known or heretofore known methods. Preferable examples include nasal drop preparations, liquid preparations, gel preparations, spray preparations, ointment preparations, cream preparations, lotion preparations, or powder preparations; more preferable examples are nasal drop preparations, liquid preparations, gel preparations, powder preparations, aerosol preparations or spray preparations, and a particularly preferable example is liquid preparations.

Nasal drop preparations of the present invention may be a liquid preparation or dry products such as a powder, and may comprise carriers or excipients, surfactants, suspending agents, mucosa-adherent bases and tonicity agents. Preferable examples of tonicity agents include sodium chloride, glycerin, sodium bisulfite, benzalkonium chloride, fluctose, citric acid, sodium citrate, sodium dihydrogen phosphate (crystal), sodium hydroxide, D-sorbitol solution, nicotinic-acid amide, concentrated glycerin, propylene glycol, benzyl alcohol, boric acid, borax, macrogol 4000, sodium hydrogen phosphate, potassium dihydrogen phosphate, and sodium dihydrogen phosphate. Examples of suspending agents include crystalline cellulose-sodium carmellose and hydroxypropyl cellulose.

A gel preparation (suspension base) may be a hydrous gel, an anhydrous gel, or a gel with a low water content comprising a gel-forming material that can swell. It may also be a hydrogel base or a lyogel base, and preferably a transparent hydrogel having an inorganic or organic polymer as abase. Similar to preparations comprising an oil or fat content, the gel itself is not absorbed by the nasal mucous membrane. Hydrogel bases have no fat and a consistency similar to that of ointment preparation, and aim at increasing the percutaneous absorbability of drugs. Lyogel bases are gelled by suspending stearyl alcohol, etc. in propylene glycol, and they have excellent absorbability by the nasal mucous membrane and hygroscopicity.

The gel preparation of the present invention may be a gel preparation made by homogenously dispersing CNP or BNP as an active ingredient into a hydrophilic gel base comprising carboxy vinyl polymer, sodium polyacrylate, sodium polyacrylate, (vinyl methyl ether/ethyl maleate) copolymer, polymethacrylate, propylene glycol, etc.

A liquid preparation means those wherein an active ingredient consisting of CNP or BNP is dissolved in a base such as alcohol, propylene glycol, polyethylene glycol or water. Preferably, it means a liquid preparation consisting of an aqueous solution wherein either CNP or BNP is dissolved in saline. In the aqueous solution preparations, a small amount of an organic base such as alcohol, propylene glycol, polyethylene glycol, etc. may be mixed, in addition to the saline.

An ointment preparation may comprise either a grease base or a water-soluble base, and both can be easily obtained in accordance with heretofore known methods. A grease base such as vaseline causes little irritation and is odorless, which is superior in protective action of the nasal mucous membrane. Water-soluble bases produce ointment preparations having a macrogol base as the main ingredient, and they have a strong action to absorb and remove aqueous discharges.

A cream preparation (emulsion base) may be an oil-in-water base (O/W) (vanishing cream) or a water-in-oil base (cold cream). An oil-in-water base has a smaller amount of oil-soluble component than water-soluble component, so that it has an advantage that the white color of the cream appears to disappear upon application. In addition, since it is easily absorbed by the nasal mucous membrane, it can be very applicable to chronic hypertrophic lesions.

A lotion preparation means a liquid external preparation wherein CNP or BNP is dissolved or homogeneously dispersed in a liquid. Since lotion preparations are in a liquid state, they are suitable for use in the mucous membrane of the nasal cavities. The form of the lotion preparations may be a suspended lotion base and an emulsion lotion.

A spray preparation refers to those wherein CNP or BNP is made into a solution, which is then sprayed by gas pressure. Sprays are convenient for application to a wide area.

As a liquid preparation, for example an aqueous solution wherein an appropriate amount of CNP or BNP is blended, saline can be used. Alternatively, an aqueous solution wherein CNP or BNP is dissolved in a buffer that can retain CNP or BNP in a stable manner can be used.

As a powder preparation, CNP or BNP can be administered in a pure dosage form or a dosage form wherein CNP or BNP is diluted with an inactive carrier. As inactive carrier, calcium carbonate or lactose can be used. At the same time, povidone and lactose can be added as a hydrophilic aid.

Since the nose has a potent discharge mechanism, administration in the form of dry powder is advantageous over liquid forms, because the duration of action is prolonged. Powders can be prepared by making fine powders through recrystallization, granulation, drying, or pulverization to a specific grain size.

Aerosol preparations are prepared as follows: CNP or BNP is pulverized to a size of preferably 5 µm or smaller, a dispersing agent is added if necessary, which is then filled in a spraying device together with a propellant while cooling. Examples of preferable dispersing agents include nonionic surfactants commercially available under the brand name of Span 80 and Span 85, amphoteric surfactants such as soybean lecithin, and natural alcohols such as oleyl alcohol. Preferable propellants include fluorinated/chlorinated lower alkanes such as chlorofluorocarbon (CFC) 11, CFC 12, CFC 114 as well as mixtures thereof.

Thus, upon production of the therapeutic preparations for rhinitis of the present invention, various types of bases, moisturizing agents, ultraviolet absorbers, alcohols, chelates, pH adjusters, preservatives, thickening agents, coloring agents, flavors, filling agents, excipients, disintegrating agents, extenders, binding agents, film forming agents, solubilizers, suspending agents, buffers, stabilizing agents, preserving agents, surfactants, antioxidative agents, dispersing agents, emulsifying agents, dissolving agents, solubilizing agents, etc. may be blended in combination. Furthermore, in addition to the principal agent CNP or BNP, various drugs such as antiphlogistic analgesics, sterilizing agents and vitamins may be appropriately blended when necessary.

Examples of excipients include lactose, corn starch, calcium phosphate, etc. Examples of binding agents include crystalline cellulose, mannitol, hydroxypropyl cellulose, hydroxypropyl methylcellulose, macrogol, etc.

Preferable liquid preparations are CNP or BNP aqueous solution preparations comprised of an appropriate amount of CNP or BNP dissolved in saline. It is possible to use a liquid preparation by filling a spraying device with it. These solution preparations may be blended with general additives, for example, sedimentation-preventing agents such as sorbitol, syrup, methylcellulose, gelatin, hydroxyl ethylcellulose, carboxy methylcellulose, aluminum stearate gel or hydrogenated food fat; emulsifying agents such as lecithin, sorbitan monooleate, and gum arabic; oily esters such as almond oil, purified coconut oil, and glycerin esters; non-aqueous media (which may include food oils) such as propylene glycol and ethyl alcohol; preservatives such as p-hydroxyl benzoic acid methyl ester, ethyl ester or propyl ester, or sorbic acid; and if necessary, general flavoring agents or coloring agents.

Here, when oral preparations of the present therapeutic preparation for rhinitis are to be produced, it is preferable to make enteric-coated drugs by coating the surface of the tablets or granules with an enteric coat, or by using enteric-coated capsules, in order to suppress disintegration of the peptide CNP or BNP by gastric acid.

Moreover, solutions may be made into, in addition to the above-mentioned aqueous solutions, aqueous or oily suspension preparations or emulsion preparations. Alternatively, they can be provided as dry pharmaceutical compositions, which can be re-dissolved into water or an appropriate medium prior to their use.

Thus, the therapeutic preparation for rhinitis of the present invention is a preparation made by blending an appropriate amount of CNP or BNP with various bases, as well as additives if necessary. Dosage form and base of the therapeutic preparation for rhinitis of the present invention can be appropriately selected depending on the symptoms and patient.

Next, production of aqueous-solution preparations as liquid preparations, and of gel preparations is described as representative examples of the present therapeutic preparations for rhinitis.

In the present invention, one preferred nasal drop preparation is an aqueous solution preparation. Such an aqueous solution preparation can be prepared as follows: for example, 0.1-1 mg of human CNP-22 (Peptide Institute, Inc.) as the principal agent is dissolved in 10 ml of saline to prepare the aqueous solution preparation with a CNP concentration of 10-100 μg/ml. Here, since the specific gravity of water is 1, the CNP concentration in this case is 10-100 μg/g by weight. The effect is insufficient when the CNP concentration is 20 μg/ml or less, but it is sufficient when the CNP concentration is 100 μg/ml; accordingly, it is not necessary to use a concentration exceeding 200 μg/ml. Preferable CNP concentration in aqueous solutions is 10-500 μg/g, more preferably 20-200 μg/g, furthermore preferably 50-200 μg/ml, and particularly preferably 50-100 μg/ml.

BNP aqueous solutions can be produced similarly to the CNP aqueous solution preparations, and preferable concentrations are the same as those of CNP aqueous solutions.

Gel preparations can be obtained by, in accordance with heretofore known or well-known methods, dissolving an appropriate amount of CNP into distilled water or saline to make an aqueous solution, and by mixing and stirring a heretofore known or well-known or commercially-available gelling agent with the solution. Preferable CNP concentrations in the gel preparations are 10-500 μg/g, more preferably 20-200 μg/g, furthermore preferably 50-200 μg/g, particularly preferably 10-100 jig/g, and even furthermore preferably 50-100 μg/g, and most preferably 30-100 μg/g.

Examples of the gelling agents consisting of macromolecular inorganic components include hydrous or water-absorbing silicates, such as aluminum silicate, for example bentonite, magnesium-aluminum silicate, and colloidal silica. As the gelling agent consisting of macromolecular organic substances, natural, semi-synthetic, or synthetic polymers may be used. Examples of natural and semi-synthetic polymers include, polysaccharides such as cellulose, starch, tragacanth, gum arabic, xanthan gum, agar-agar, gelatin, alginic acid and its salts, for example sodium alginate and its derivatives, loweralkyl cellulose, for example methyl cellulose or ethyl cellulose, carboxy- or hydroxyl-lower-alkyl cellulose, for example carboxymethyl cellulose, or hydroxypropyl cellulose, etc.

Examples of synthetic gelling agents include polyvinyl alcohol, polyvinyl pyrrolidone, polyacrylic acid or polymethacrylic acid, etc. Only one kind of these gelling agents, or a mixture of two or more kinds of these may be used.

If necessary, a percutaneous absorption aid may be added. Examples of the percutaneous absorption aid include, for example, limonene, menthol, salicylic acid, hyaluronic acid, oleic acid, N,N-diethyl-m-toluamide, n-butyl stearate, benzyl alcohol, isopropyl myristate, isopropyl palmitate, polypropylene glycol, crotamiton, diethyl sebacate, N-methyl pyrrolidone, N-ethyl pyrrolidone, lauryl alcohol, etc. In addition, an antiseptic agent and an antioxidant may be added if necessary.

The concentration of CNP or BNP in the therapeutic preparation for rhinitis may be appropriately selected with consideration given to symptoms, age, and dosage form, etc.

Preferable concentrations of CNP or BNP are, for nasal drop preparations such as solutions, gel preparations, lotion preparations, and aerosols, etc., 10-500 μg/g, and more preferably 20-200 μg/g. For younger patients and patients with sensitive skin, those with a concentration of 20-100 μg/g are preferably used. Preferable CNP or BNP concentrations in the gel preparations are 10-100 μg/g, and particularly preferably 30-100 μg/g. Preferable CNP or BNP concentrations in the solutions are 20-200 μg/ml, and particularly preferably 50-200 μg/ml.

The number of applications and the duration of application of the present therapeutic preparation for rhinitis differ depending on symptoms, age and dosage form, etc.; normally, once or twice a day for 2 to 7 days of application is sufficient.

Hereinafter, the present invention is explained with reference to examples. However, the present invention is not limited to these examples.

Example 1

1. Production of CNP Nasal Solution:

A 1000 μg/ml CNP liquid preparation was prepared by dissolving 3 mg of human CNP-22 (Peptide Institute, Inc.) as the principal agent in 3 ml of saline. 100 μl of the obtained 1000 μg/ml CNP solution preparation was diluted with 900 μl of saline to prepare the CNP nasal solution preparation with a CNP concentration of 100 μg/ml. Similarly, the CNP nasal solution preparation with a CNP concentration of 50 μg/ml was prepared by diluting 50 μl of the 1000 μg/ml CNP solution preparation with 950 μl of saline. Furthermore, similarly, the CNP nasal solution preparation with a CNP concentration of 200 μg/ml was prepared by diluting 200 μl of the 1000 μg/ml CNP solution preparation with 800 μl of saline.

2. Production of Nasal Drop Preparations Consisting of CNP Nasal Solution:

Three kinds of CNP nasal solution preparations with concentrations of 100 μg/ml, 50 μg/ml, and 200 μg/ml obtained as above were used to fill a metered-dose nasal spraying device (Astellas Pharma, Inc.; a metered-dose nasal spraying device for Intal nasal solution was used), and the device was adjusted so that the amount of a solution delivered by one spray is 130 μl. Accordingly, the amount of CNP contained in one spray of solution of the CNP nasal solutions with 100 μg/ml, 50 μg/ml, and 200 μg/ml are 13 μg, 6.5 μg, and 26 μg, respectively.

3. Production of BNP Nasal Solution Preparation:

A 1000 μg/ml BNP solution preparation was prepared by dissolving 3 mg of human BNP-32 (Peptide Institute, Inc.) as the principal agent in 3 ml of saline. 100 μl of the obtained 1000 μg/ml BNP solution preparation was diluted with 900 μl of saline to prepare the BNP nasal solution preparation with a BNP concentration of 100 μg/ml. Similarly, the BNP nasal solution preparation with a BNP concentration of 50 μg/ml was prepared by diluting 50 μl of the 1000 μg/ml BNP solution preparation with 950 μl of saline. Furthermore, similarly, the BNP nasal solution preparation with a BNP concentration of 200 μg/ml was prepared by diluting 200 μl of the 1000 μg/ml BNP solution preparation with 800 μl of saline.

4. Production of Nasal Drop Preparations Consisting of BNP Nasal Solution:

Three kinds of BNP nasal solution preparations with concentrations of 100 μg/ml, 50 μg/ml, and 200 μg/ml obtained as above were used to fill a metered-dose nasal spraying device (Astellas Pharma, Inc.; a metered-dose nasal spraying device for Intal nasal solution was used), and the device was adjusted so that the amount of a solution preparation delivered by one spray is 130 μl. Accordingly, the amount of BNP contained in one spray of solution for the BNP nasal solution preparations with 100 μg/ml, 50 μg/ml, and 200 μg/ml are 13 μg, 6.5 μg, and 26 μg, respectively.

5. Production of ANP Nasal Solution:

For comparative tests, a 500 μg/ml ANP solution preparation was prepared by dissolving 0.5 mg of human ANP-28 (Peptide Institute, Inc.) in 1 ml of saline. 1 ml of the obtained 500 μg/ml ANP solution was diluted with 9 ml of saline to prepare the ANP nasal solution preparation with an ANP concentration of 50 μg/ml.

6. Production of Nasal Drop Preparations Consisting of ANP Nasal Solution:

The ANP nasal solution preparation with an ANP concentration of 50 μg/ml obtained as above was used to fill a metered-dose nasal spraying device (Astellas Pharma, Inc.; a metered-dose nasal spraying device for Intal nasal solution was used), and the device was adjusted so that the amount of a solution preparation delivered by one spray is 130 μl. Accordingly, the amount of ANP contained in one spray of solution is 6.5 μg.

Example 2

Diagnosis, evaluation of symptoms, and examination of the CNP nasal drop preparations, BNP nasal drop preparations and ANP nasal drop preparation were performed as follows.

1. Subjects and Diagnosis

The subjects are patients in whom conventional external medicines such as steroids are not sufficiently effective, or patients in whom the use of steroids must be avoided due to local side effects such as nasal irritation and dryness. Diagnosis and treatment of these subjects were performed by the present applicant as a medical doctor.

2. Evaluation of Symptoms

Severity evaluation of symptoms of allergic rhinitis was performed, in principle, in accordance with "Guidelines for medical care of nasal allergies, 2009 edition" (edited by the committee for creation of guidelines for medical care of nasal allergies), by classifying into 5 stages as shown below. Here, "mixed type" refers to the cases wherein both of the sneezing attack or rhinorrhea and the nasal occlusion were presented with the same severity.

TABLE 2

| Degree and severity | Sneezing attack or rhinorrhea (determined by item with higher score) | | | | |
| --- | --- | --- | --- | --- | --- |
| | − | + | 2+ | 3+ | 4+ |
| Nasal occlusion 4+ | Most severe (Nasal occlusion type) | Most severe (Nasal occlusion type) | Most severe (Nasal occlusion type) | Most severe (Nasal occlusion type) | Most severe (mixed type) |

TABLE 2-continued

| Degree and severity | Sneezing attack or rhinorrhea (determined by item with higher score) | | | | |
|---|---|---|---|---|---|
| | − | + | 2+ | 3+ | 4+ |
| 3+ | Severe (Nasal occlusion type) | Severe (Nasal occlusion type) | Severe (Nasal occlusion type) | Severe (mixed type) | Most severe (sneezing/ rhinorrhea type) |
| 2+ | Moderate (Nasal occlusion type) | Moderate (Nasal occlusion type) | Moderate (mixed type) | Severe (sneezing/ rhinorrhea type) | Most severe (sneezing/ rhinorrhea type) |
| + | Mild (Nasal occlusion type) | Mild (mixed type) | Moderate (sneezing/ rhinorrhea type) | Severe (sneezing/ rhinorrhea type) | Most severe (sneezing/ rhinorrhea type) |
| − | No symptoms | Mild (sneezing/ rhinorrhea type) | Moderate (sneezing/ rhinorrhea type) | Severe (sneezing/ rhinorrhea type) | Most severe (sneezing/ rhinorrhea type) |

In the above table, evaluation scores for sneezing fit, rhinorrhea and nasal occlusion are as described in the table below.

TABLE 3

| | − | + | 2+ | 3+ | 4+ |
|---|---|---|---|---|---|
| Sneezing attack (average number of sneezing attacks per day) | 0 | 1-5 | 6-10 | 11-20 | 21 or more |
| Nasal drip (average number of nose blows a day) | 0 | 1-5 | 6-10 | 11-20 | 21 or more |
| Nasal occlusion | 0 | No mouth breathing, but with nasal occlusion | Strong occlusion, breathing with the mouth several times a day | Very strong occlusion, with mouth breathing for a considerable amount of time a day | Nose is completely occluded all day. |
| Degree of disturbance in daily life | 0 | Almost no disturbance | Between (+) and (3+) | Cannot have normal daily life because of disturbance | Normal daily life is impossible |

3. Test Method of Nasal Solution Preparation

Administration tests of the nasal solution preparations of the present invention were performed by, in principle, spraying the CNP nasal solution, BNP nasal solution or ANP nasal solution used to fill a nasal spraying device twice a day at awakening time and before bedtime, with one spray in each nostril at each time. Accordingly, the amount of application of CNP, BNP or ANP per one spray for the 100 µg/ml CNP nasal solution, BNP nasal solution, and ANP nasal solution corresponds to 13 µg. Similarly, the amounts of application of CNP, BNP or ANP per one spray for the 50 µg/ml and 200 µg/ml CNP/BNP/ANP solutions correspond to 6.5 µg and 26 µg, respectively.

Example 3

Diagnosis of Each Case

Prior to the application of CNP preparations, BNP preparations or ANP preparation, the subjects' history was obtained, scratch tests for allergens were performed and diagnosis was made. Tables 4-7 show the results of the subjects' history taking, diagnosis, i.e., sex, age, past history, family history, scratch test result, diagnostic finding, and symptom evaluation of the subject in each case.

Example 4

CNP Dosage-Finding Study

The after-mentioned subject of Case 10 was enrolled in the study, and the 100 µg/ml CNP nasal solution was applied once a day for 7 days consecutively, then after 14 days of discontinuation, the 50 µg/ml CNP nasal solution was tested. As a result, the time required for the manifestation of the effect is approximately 20 min, that is, compared to the 100 µg/ml CNP nasal solution, approximately twice as long a time is required for the manifestation of the drug efficacy, with a slightly lower degree of improvement of nasal occlusion. Here, the 200 µg/ml CNP nasal solution showed significant effects on rhinitis without irritation, but the effects were not doubled compared to the case of 100 µg/ml CNP nasal solution.

BNP Dosage-Finding Study

A dosage-finding study was also performed for BNP, and results similar to those for CNP were obtained.

Example 5

Results of administration of CNP preparations are summarized in Tables 4 and 5 and FIG. 2, and details are described below as test examples 1-10.

TABLE 4

| | Case 1 | Case 2 | Case 3 | Case 4 | Case 5 |
|---|---|---|---|---|---|
| Sex | Female | Female | Female | Male | Female |
| Age | 48 years old | 39 years old | 32 years old | 23 years old | 24 years old |
| Severity level | Severe | Severe | Severe | Severe | Severe |

TABLE 4-continued

|  | Case 1 | Case 2 | Case 3 | Case 4 | Case 5 |
| --- | --- | --- | --- | --- | --- |
| Disease type | Mixed | Sneezing/rhinorrhea | Mixed | Nasal occlusion | Mixed |
| Family history | Child; atopic dermatitis, allergic rhinitis | Child; atopic dermatitis | Mother; atopic dermatitis | Mother; atopic dermatitis | Younger sister; atopic dermatitis |
| Past history | Atopic dermatitis | Atopic dermatitis | Atopic dermatitis | Child asthma | Atopic dermatitis |
| Scratch test | House dust: 3+ Mite: 3+ Cedar: — Orchard grass: — Ragweed: — | House dust: 2+ Mite: 2+ Cedar: 2+ Orchard grass: 3+ Ragweed: 1+ | House dust: 1+ Mite: 1+ Cedar: 1+ Orchard grass: 2+ Ragweed: 1+ | House dust: 3+ Mite: 3+ Cedar: — Orchard grass: — Ragweed: — | House dust: 3+ Mite: 3+ Cedar: 3+ Orchard grass: 2+ Ragweed: 2+ |
| Diagnostic finding |  |  |  |  |  |
| Nasal drip (average number of nose blows a day) | (11-20) | A lot of nasal drip, so she uses a pile of tissue paper for nose blowing (approx. 20) | (11-20) | (1-5) | (11-20) |
| Nasal occlusion | Very strong nasal occlusion, with mouth breathing for a considerable amount of time a day. | No mouth breathing, but has nasal occlusion. | Very strong nasal occlusion, and she is unable to smell well. | Very strong nasal occlusion, with mouth breathing for a considerable amount of time a day. | Very strong nasal occlusion, with mouth breathing for a considerable amount of time a day. |
| Effects of steroid nasal spray | Not used due to nasal irritation. | Nasal irritation, itching, sneezing, and rhinorrhea rather worsened, and no subjective improvement noticed. | Nasal irritation, and dryness sensation as if the nose is in contact with the back of the throat existed; no satisfactory effects. | Not used because of withdrawal difficulty due to long term use of systemic steroids. | Not used due to nasal irritation and dryness. |
| Dosage form | CNP nasal solution preparation | CNP nasal solution preparation | CNP nasal solution preparation | CNP nasal solution preparation | CNP nasal solution preparation |
| Dosage | 100 μg/ml | 100 μg/ml | 100 μg/ml | 100 μg/ml | 100 μg/ml |
| Number of nasal applications | Morning + before bedtime | Once in the morning | Once in the morning | Once a day | Once a day |
| Number of days applied | 2 days | 3 days | 7 days | 4 days | 1 day |
| Symptom improvement by initial nasal application | 15 min later, rhinorrhea was relieved and nasal occlusion was improved. | Nasal itching disappeared immediately after spraying, and rhinorrhea was relieved 10 min later. | 5 min later, nasal occlusion disappeared and rhinorrhea was relieved. | 5 to 10 min later, nasal occlusion sensation disappeared. | 20 min later, nasal occlusion sensation was improved and rhinorrhea was relieved. |
| Progress and symptom improvement | Symptoms reduced by spraying twice a day for 2 days including the application at the first visit, and both rhinorrhea and nasal occlusion were markedly improved. The effects lasted for 2-3 days after discontinuation of the application, without symptoms. | The sinus was not congested and rhinorrhea stopped by application once a day. The effects lasted all day. After discontinuation of the application, effects lasted for 2-3 days, and watery nasal drip was suppressed. | Nasal occlusion sensation disappeared by continuous application once a day in the morning, and rhinorrhea was completely relieved 3 days later. After continuous application once a day for one week, application was discontinued, but the effects were maintained for a long time thereafter. | The effects lasted all day, and the nasal passages opened and the subject was able to breathe easily. After 4 days of application, the application was discontinued, but the effects lasted for approximately 3 days thereafter. | Both rhinorrhea and nasal occlusion were alleviated for one day. |
| Symptom improvement | Severe → mild | Severe → mild | Severe → mild | Severe → mild | Severe → mild |

TABLE 5

|  | Case 6 | Case 7 | Case 8 | Case 9 | Case 10 |
| --- | --- | --- | --- | --- | --- |
| Sex | Female | Female | Female | Male | Female |
| Age | 37 years old | 39 years old | 39 years old | 21 years old | 55 years old |
| Severity level | Severe | Severe | Moderate | Severe | Severe |
| Disease type | Mixed | Mixed | Mixed | Nasal occlusion | Mixed |
| Family history | Mother and elder sister; atopic dermatitis | Child; atopic dermatitis | None | Mother; atopic dermatitis | Child; atopic dermatitis |
| Past history | Atopic dermatitis | Atopic dermatitis | Child asthma, atopic dermatitis, sinusitis | Atopic dermatitis, allergic conjunctivitis | Atopic dermatitis |
| Scratch test | House dust: 3+<br>Mite: 3+<br>Cedar: —<br>Orchard grass: —<br>Ragweed: — | House dust: —<br>Mite: 2+<br>Cedar: —<br>Orchard grass: 3+<br>Ragweed: — | House dust: 2+<br>Mite: 3+<br>Cedar: 2+<br>Orchard grass: 1+<br>Ragweed: —<br>Cat hair: 3+ | House dust: 2+<br>Mite: 3+<br>Cedar: 2+<br>Orchard grass: 3+<br>Ragweed: 1+ | House dust: 1+<br>Mite: 2+<br>Cedar: 2+<br>Orchard grass: 3+<br>Ragweed: 2+ |
| Diagnostic finding |  |  |  |  |  |
| Nasal drip (average number of nose blows a day) | (11-20) | (11-20) | (6-10) | (1-5) | (11-20) |
| Nasal occlusion | Very strong nasal occlusion, with mouth breathing for a considerable amount of time a day. | Very strong nasal occlusion, with mouth breathing for a considerable amount of time a day. | Strong nasal occlusion, with mouth breathing several times a day. | Very strong nasal occlusion, with mouth breathing for a considerable amount of time a day. | Strong nasal occlusion, always having aural fullness. |
| Effects of steroid nasal spray | Not used due to nasal irritation. | Not used due to nasal irritation, sneezing and runny nose. | Not used because she suffered from sinusitis 1.5 years ago. | Has used in the past, but nasal occlusion did not improve sufficiently. | Nasal occlusion did not improve sufficiently and effects did not last for a long time. |
| Dosage form | CNP nasal solution preparation | CNP nasal solution preparation | CNP nasal solution preparation | CNP nasal solution preparation | CNP nasal solution preparation |
| Dosage | 100 µg/ml | 100 µg/ml | 100 µg/ml | 100 µg/ml | 100 µg/ml |
| Number of nasal applications | Morning + before bedtime (2 times) | Once a day | Once a day | Once a day | Once a day |
| Number of days applied | 5 days | 1 day | 1 day | 1 day | 7 days |
| Symptom improvement by initial nasal application | 1 hr later, nasal occlusion was markedly improved and she could breathe easily and sleep well. | Nasal passages opened immediately after the application and nasal occlusion was markedly improved 10 min later. | Nasal passages opened immediately after the application and nasal occlusion was markedly improved 10 min later, nasal drip stopped 20 min later. | Nasal passages opened immediately after the nasal application and rhinorrhea and nasal occlusion were markedly improved 25 min later, then rhinorrhea stopped. | 10 min later, nasal occlusion and runny nose completely stopped. Aural fullness also disappeared. |
| Progress and symptom improvement | By application once a day, nasal itching and a nasal occlusion sensation disappeared and she no longer needed to blow her nose. After application twice a day, in the morning and before bedtime for a total of 5 days, the application was discontinued, but the effects lasted for 4-5 days. | By application once a day, effects lasted until the next day and improvement in rhinorrhea and nasal occlusion was maintained. | By application once a day, effects lasted until the next day, and rhinorrhea and nasal occlusion were improved to a barely-troublesome level. | The effects lasted all day by application once in the late afternoon, and for 3 days thereafter, runny nose reduced to a barely-troublesome level without any treatment. During this period, internal application of antihistamine drugs was not necessary. | The effects lasted all day by application once a day and nasal symptoms stayed improved, with watery nasal drip stopped and nasal passages feeling open. After discontinuation of the application, the effects lasted for approximately 1 week. |
| Symptom improvement | Severe → mild | Severe → mild | Moderate → mild | Severe → mild | Severe → mild |

Test Example 1 (Case 1)

The subject is a 48-year-old female who is a patient with severe mixed-type rhinitis. She has a past history of atopic dermatitis, and her child also suffers from atopic dermatitis and allergic rhinitis. Scratch test results are: house dust 3+ and mite 3+. She has very strong nasal occlusion, with mouth breathing for a considerable amount of time a day, and also has strong watery nasal drip. She is unable to use steroid nasal sprays due to nasal irritation.

As a preliminary test, the CNP nasal solution with a concentration of 100 µg/ml obtained in Example 1 was sprayed once into each nostril of the subject (the amount of CNP administered to one nasal cavity was 13 µg). As a result, 15 min later, rhinorrhea was relieved and nasal occlusion was improved. Permeability of the CNP nasal solution was good without nasal irritation, and side effects such as local irritation symptoms were not observed.

Therefore, in the morning and before bedtime on the next day (a total of two times), the present CNP nasal solution was sprayed once in each nostril, then the symptoms reduced and rhinorrhea and nasal occlusion were markedly improved for the whole day of day 3. After discontinuation of the nasal spray, the effects persisted for 2-3 days without symptoms.

Test Example 2 (Case 2)

The subject is a 39-year-old female who is a patient with severe sneezing/rhinorrhea-type rhinitis. She has a past history of atopic dermatitis, and her child also suffers from atopic dermatitis. Scratch test results are: house dust 2+, mite 2+, cedar 2+, orchard grass 3+, and ragweed 1+. She is a severe case having both symptoms of nasal occlusion, with sneezing and watery nasal drip requiring a pile of tissue paper, and is taking second-generation antihistamine drugs every day. With steroid nasal sprays, nasal irritation, nasal itching, sneezing and rhinorrhea become worsened, and subjective effects of improvement are not noted. Similar to test example 1, the CNP nasal solution with a concentration of 100 µg/ml obtained in Example 1 was sprayed once into each nostril of the subject (the amount of CNP administration in one nasal cavity was 13 µg). As a result, nasal itching disappeared immediately after the spraying, and rhinorrhea was relieved after 10 min. The CNP nasal solution had a good permeability without nasal irritation, and no local side effects were observed. By use only once a day, the nose was not congested and absolutely no rhinorrhea was observed. The effects lasted for a whole day.

Also on the next morning, absolutely no rhinorrhea was observed. To be safe, the present CNP nasal solution was sprayed once into each nostril in the morning. As a result, the nose was not congested and no rhinorrhea was observed during this day. She said that she almost had forgotten about rhinitis, and second-generation antihistamine drugs had not been necessary.

These results demonstrated that the CNP nasal solution of the present invention is superior in persistence, absorbability and fast-acting property, and that sufficient effects can be obtained by spraying only once a day.

Test Example 3 (Case 3)

The subject is a 32-year-old female who is a patient with severe mixed-type rhinitis. She has a past history of atopic dermatitis, and her mother also suffers from atopic dermatitis. Scratch test results are: house dust 1+, mite 1+, cedar 1+, orchard grass 2+, and ragweed 1+. This subject has a very strong nasal occlusion, and is unable to smell. She also has severe watery rhinorrhea. Steroid nasal spray induced nasal irritation and dryness sensation as if the nose was in contact with the back of the throat, and no satisfactory effects were obtained except that runny nose slightly reduced after the application.

Similar to test example 1, the CNP nasal solution with a concentration of 100 µg/ml obtained in Example 1 was sprayed once into each nostril of the subject (the amount of CNP administered in one nasal cavity was 13 µg). As a result, the nasal occlusion sensation disappeared and rhinorrhea was relieved 5 min later. No local irritation symptoms were observed. Thereafter, spraying once a day in the morning was continued, then nasal occlusion sensation disappeared and she became able to smell, watery nasal drip was improved, and rhinorrhea was completely relieved 3 days later. No local side effects such as irritation, as well as no systemic side effects such as drowsiness were observed. For a week, the effects lasted for the whole day by application once in the morning; an anti-allergic agent was orally taken on day 1, but this administration was not necessary from day 2 and thereafter. Application was discontinued after one week, but the effects lasted for more than 2 weeks thereafter. This finding demonstrated that the CNP nasal solution of the present invention is excellent in fast-acting property, absorbability and persistence, and that sufficient effects can be obtained by spraying only once a day.

Test Example 4 (Case 4)

The subject is a 23-year-old male who is a patient with severe nasal-occlusion-type rhinitis. He has a past history of childhood asthma, and his mother suffers from atopic dermatitis. Scratch test results are: house dust 3+, and mite 3+. This subject has a very strong tendency of nasal occlusion, with mouth breathing for a considerable amount of time a day. In addition, because of the withdrawal difficulty symptoms due to long-term use of systemic steroids, this subject must avoid the use steroids.

Similar to test example 1, the CNP nasal solution with a concentration of 100 µg/ml obtained in Example 1 was sprayed once into each nostril of the subject (the amount of CNP administration in one nasal cavity was 13 µg). As a result, nasal occlusion sensation disappeared within 5 to 10 min. The effects lasted for one day, and he was able to breathe easily with open nasal passages. After the application of once a day for 4 days, the application was discontinued, but the effects lasted for about 3 days thereafter.

Similar to the above test cases, the CNP nasal solution has a good permeability without irritation or local side effects. These facts are also observed in the following test examples.

Thus, the CNP nasal solution of the present invention has remarkable effects, and can be a great relief for patients with rhinitis who must avoid the use of steroid preparations.

Test Example 5 (Case 5)

The subject is a 24-year-old female who is a patient with severe mixed-type rhinitis. She has a past history of atopic dermatitis, and her younger sister also suffers from atopic dermatitis. Scratch test results are: house dust 3+, mite 3+, cedar 3+, orchard grass 2+, and ragweed 2+. The subject goes through mouth breathing for a considerable amount of time a day, and has a very strong tendency of nasal occlusion, with severe nasal drip. She dose not use steroid nasal sprays because of nasal irritation and dryness.

Similar to test example 1, the CNP nasal solution with a concentration of 100 µg/ml obtained in Example 1 was sprayed once into each nostril of the subject (the amount of CNP administered in one nasal cavity was 13 µg). As a result, nasal occlusion sensation was improved 20 min later, and rhinorrhea was relieved. The effects lasted for one day, and alleviation of the nasal occlusion and rhinorrhea persisted on the next day and thereafter.

Test Example 6 (Case 6)

The subject is a 37-year-old female who is a patient with severe mixed-type rhinitis. She has a past history of atopic dermatitis, and her mother and elder sister also suffer from atopic dermatitis. Scratch test results are: house dust 3+ and mite 3+. This subject has, similar to Case 5, mouth breathing for a considerable amount of time a day, and has a very strong tendency of nasal occlusion, with severe nasal drip. The subject was suffering from strong nasal occlusion and sneezing at night, as well as nasal itching. She dose not use steroid nasal sprays because of nasal dryness.

The CNP nasal solution with a concentration of 100 µg/ml obtained in Example 1 was sprayed once into each nostril of the subject before bedtime (the amount of CNP administration in one nasal cavity was 13 µg); 1 hr later, nasal occlusion was markedly improved and she was able to breathe easily and sleep well with well-opened nasal passages even in the early hours of the morning, so she reported.

Moreover, the CNP nasal solution of the invention is re-sprayed once into each nostril on the next morning, following the administration previous night, then nasal itching and nasal occlusion sensation disappeared for the whole day. Watery nasal drip was improved to a condition in which blowing of nose was not required. No local irritation symptoms were observed. Thereafter, because the symptoms had stabilized by the twice a day application for 5 days, the application was discontinued. The effects persisted for 4-5 days after the discontinuation, and the improved states of nasal itching, nasal occlusion and rhinorrhea were maintained.

Test Example 7 (Case 7)

The subject is a 39-year-old female who is a patient with severe mixed-type rhinitis. She has a past history of atopic dermatitis, and her child also suffers from atopic dermatitis. Scratch test results are: house dust -, mite 2+, cedar -, orchard grass 3+, and ragweed -. This subject, similar to Case 6, breathes through her mouth for a considerable amount of time a day, and has a very strong tendency of nasal occlusion, with severe nasal drip. In particular the subject was suffering from severe rhinorrhea, nasal occlusion and sneezing in the early hours of the morning, as well as nasal itching. She had nasal irritation against steroid nasal sprays, and because sneezing and runny nose rather worsened, she was unable to use steroids; when she orally took second-generation antihistamine drugs, she tends to feel sluggish; therefore, the use of antihistamine drugs must be avoided as much as possible.

Under such conditions, the CNP nasal solution with a concentration of 100 µg/ml obtained in Example 1 was sprayed once into each nostril of the subject (the amount of CNP administered in one nasal cavity was 13 µg); immediately after spraying, the nasal passages opened, and the nasal occlusion was markedly improved after 10 min. She also reported that she was able to breathe easily. Watery nasal drip, that had continuously discharged if the nostrils were not packed with tissue paper, stopped. With an application once a day, the effects lasted until the next day, and the improvements in nasal occlusion and rhinorrhea were maintained.

Thus, the CNP nasal solution of the present invention is a relief for rhinitis patients with whom the use of conventional steroids and antihistamine drugs should be avoided or inapplicable.

Test Example 8 (Case 8)

The subject is a 39-year-old female who is a patient with moderate mixed-type rhinitis. She has a past history of atopic dermatitis, childhood asthma and sinusitis, but her family members do not suffer from any of these diseases or allergic rhinitis. Scratch test results are: house dust 2+, mite 3+, cedar 2+, orchard grass 1+, ragweed -, and cat hair 3+. This subject goes through mouth breathing several times a day, and has a strong tendency of nasal occlusion. She did not use steroids because she had suffered from sinusitis one and half years ago.

The CNP nasal solution with a concentration of 100 µg/ml obtained in Example 1 was sprayed once into each nostril of this subject (the amount of CNP administered in one nasal cavity was 13 µg); as a result, the nasal passages opened immediately after spraying, and the nasal occlusion was markedly improved after 10 min, so that she could breathe easily. 20 min later, watery nasal drip stopped. Moreover, she reported that she could breathe easily.

The effects lasted for a whole day by application once a day, and both nasal occlusion and rhinorrhea were improved to a barely-troublesome level.

Test Example 9 (Case 9)

The subject is a 21-year-old male who is a patient with severe nasal-occlusion-type rhinitis. He has a past history of atopic dermatitis and allergic conjunctivitis, and his mother also suffers from atopic dermatitis. Scratch test results are: house dust 2+, mite 3+, cedar 2+, orchard grass 3+, and ragweed 1+. This subject, similar to Case 7, breathes through his mouth for a considerable amount of time a day, and has a very strong tendency of nasal occlusion. He had used steroids in the past, but nasal occlusion was not improved sufficiently. Nasal drip was not so severe.

The CNP nasal solution with a concentration of 100 µg/ml obtained in Example 1 was sprayed once into each nostril of this subject (the amount of CNP administered in one nasal cavity was 13 µg); as a result, immediately after spraying, the nasal passages opened, and the nasal occlusion was markedly improved and rhinorrhea was relieved after 25 min without any irritation symptoms. As a result of nasal application of once at early evening, the effects lasted for one day and thereafter runny nose almost reduced to a barely-troublesome level for 3 days without any additional treatment, and blowing of his nose was hardly required. During this time, internal administration of antihistamine drugs was not necessary.

Test Example 10 (Case 10)

The subject is a 55-year-old female who is a patient with severe mixed-type rhinitis. She has a past history of atopic dermatitis, and her child also suffers from atopic dermatitis. Scratch test results are: house dust 1+, mite 2+, cedar 2+, orchard grass 3+, and ragweed 2+. This subject has a strong nasal occlusion, and always has aural fullness. Oral steroids and steroid sprays were applied to this subject three times a day, but the effects on the nasal occlusion were not sufficient, and the durability of the effects was poor, while improvement in rhinorrhea was insufficient. Upon application of steroid sprays, she had a headache with a feeling of heaviness from the back of the nose to the head and drowsiness.

The CNP nasal solution with a concentration of 100 µg/ml obtained in Example 1 was sprayed once into each nostril of this subject (the amount of CNP administered in one nasal cavity was 13 µg); as a result, nasal occlusion and runny nose stopped completely without irritation symptoms after 10 min. Thereafter, the CNP nasal solution of the invention was applied twice in the morning and before bedtime without taking steroids internally, then nasal occlusion and rhinorrhea were markedly improved, and aural fullness also disappeared. The effects lasted for a whole day with application once daily thereafter, and nasal symptoms were markedly improved, with runny nose stopped and nasal occlusion suppressed with a feeling of open nasal passages.

It was not necessary to use internal steroids or injections which had previous been continuously used. The application was discontinued after 7 days of application of the 100 µg/ml CNP nasal solution, but the effects lasted for approximately 1 week and the condition of reduced nasal occlusion and rhinorrhea was maintained. After 14 days of discontinuation, the application of the 50 µg/ml CNP nasal solution at an interval of once a day was started and continued for 5 days; then, nasal occlusion was relieved 20 min after the nasal spraying, and rhinorrhea was also improved to the level of 3 to 4 times a day of nose blowing. Moreover, aural fullness had disappeared. These effects lasted for 3-4 days after discontinuation of the application.

Example 6

The results of the use of BNP preparations are summarized in Table 6 and FIG. 3, and details are described below as test examples 11-16.

TABLE 6

| | Case 11 | Case 12 | Case 13 | Case 14 | Case 15 | Case 16 |
|---|---|---|---|---|---|---|
| Sex | Female | Female | Female | Female | Female | Male |
| Age | 42 years old | 21 years old | 28 years old | 46 years old | 45 years old | 35 years old |
| Severity level | Most severe | Moderate | Most severe | Most severe | Severe | Most severe |
| Disease type | Sneezing/rhinorrhea | Mixed | Nasal occlusion | Mixed | Sneezing/rhinorrhea | Mixed |
| Family history | Child; allergic rhinitis, atopic dermatitis | Father; allergic rhinitis | Younger sister; allergic rhinitis, atopic dermatitis, | Child; allergic rhinitis | Child; allergic rhinitis, atopic dermatitis | Father, elder sister, child; allergic rhinitis |
| Past history | Atopic dermatitis, allergic conjunctivitis | Atopic dermatitis | Atopic dermatitis | Atopic dermatitis, allergic conjunctivitis | Atopic dermatitis | Allergic conjunctivitis |
| Scratch test | House dust: 2+ Mite: 2+ Cedar: − Orchard grass: 3+ Ragweed: 2+ | House dust: 1+ Mite: 2+ Cedar: 3+ Orchard grass: 1+ Ragweed: 1+ | House dust: 1+ Mite: 2+ Cedar: 3+ Orchard grass: 3+ Ragweed: 2+ | House dust: 2+ Mite: 2+ Cedar: 3+ Orchard grass: 3+ Ragweed: 2+ | House dust: 2+ Mite: 3+ Cedar: 1+ Orchard grass: 2+ Ragweed: 1+ | House dust: − Mite: 1+ Cedar: 2+ Orchard grass: 3+ Ragweed: 1+ |
| Diagnostic finding | | | | | | |
| Nasal drip (average number of nose blows a day) | Constant runny nose (21 or more) | (approx. 10) | Runny nose does not stop all day (21 or more) | Constant watery rhinorrhea if the nostrils were not packed (21 or more) | Watery nasal drip discharges continuously and perennially. (approx. 20) | Watery nasal drip continuously discharges so that he uses 2 boxes of tissue paper per day. (21 or more) |
| Nasal occlusion | Has mouth breathing only at night due to nasal occlusion. | Due to strong nasal occlusion, mouth breathing, at intervals of the day. | Almost no mouth breathing, but has nasal occlusion. | Fairly strong occlusion, with mouth breathing for a considerable amount of time a day. | Almost no nasal occlusion (less than +) | Completely occluded all day. |
| Effects of steroid nasal spray/local side effects | She never felt the effects, having strong local dryness with pain. | At the time of worsening of symptoms, sufficient effects were not obtained by steroid nasal application, especially for rhinorrhea. | She had irritation with tight-stretched feeling of nasal mucosa and dryness; therefore she had no satisfactory therapeutic effects. | Completely no effects by steroid nasal solutions; having local dryness sensation. | She has strong nasal irritation, and watery nasal drip increases from that before the nasal application. | He tended to show steroid resistance, so that steroids became ineffective from the second application. He also had strong irritation symptoms. |
| Dosage form | BNP nasal solution preparation | BNP nasal solution preparation | BNP nasal solution preparation | BNP nasal solution preparation | BNP nasal solution preparation | BNP nasal solution preparation |
| Dosage | 50 µg/ml | 50 µg/ml | 100 µg/ml | 50 µg/ml | 200 µg/ml | 50 µg/ml |
| Number of nasal applications | Once in the morning, or twice in the morning and at night | Twice in the morning and at night | Once in the morning | Once before bedtime | Once a day | Once in the morning, or twice in the morning and at night |
| Number of days applied | 5 days | 7 days | 1 day | 4 days | 2 days | 5 days |

TABLE 6-continued

|  | Case 11 | Case 12 | Case 13 | Case 14 | Case 15 | Case 16 |
| --- | --- | --- | --- | --- | --- | --- |
| Symptom improvement by initial nasal application | 10 min later, the BNP solution permeated the nasal mucosa and symptoms reduced and watery nasal drip was improved. | Watery rhinorrhea stopped 10 min later and nasal occlusion sensation improved 20 min later. | Runny nose stopped 30 min later. Sneezing also stopped 1 hr after the nasal spraying. | The nose felt relieved 5 min later, and nasal passages opened 15 min later, with marked improvement in rhinorrhea; nasal occlusion was markedly improved 30 min later and itching in the throat was also relieved. | Nasal drip stopped 10 min later. She had no irritation and no uncomfortable feeling. | Watery nasal drip and itching stopped 10 min later. No irritation symptoms. |
| Progress and symptom improvement | Symptoms can be relived by application once or twice a day. Absolutely no local irritation symptoms. | As a result of continuous application twice a day for 1 week, watery rhinorrhea and nasal occlusion were improved; therefore, the application was discontinued. Thereafter, the symptoms did not reappear for 4-5 days, and a reduced state was maintained. | The effects lasted for half a day thereafter, and a runny nose began at about 9 o'clock at night. | By nasal spraying once before bedtime, the effects lasted for 3-4 days; thereafter application once before bedtime every 3-4 days maintained the condition with improved rhinorrhea, nasal occlusion and itching of the eyes. | Without combined use of internal antihistamine drugs, the effect of the stoppage of nasal drip lasted all day, and watery nasal drip could be relived by application once a day the next day. | By application twice in the morning and night, nasal occlusion was improved, and internal administration of antihistamine drugs was unnecessary. After discontinuation of the application, the effects to relieve rhinorrhea and nasal occlusion lasted for 7 days. |
| Symptom improvement | Most severe → mild | Moderate → mild | Most severe → mild | Most severe → moderate | Severe → mild | Most severe → mild |

Test Example 11 (Case 11)

The subject is a 42-year-old female who is a patient with most severe sneezing/rhinorrhea-type rhinitis. She has a past history of atopic dermatitis and allergic conjunctivitis, and her child suffers from allergic rhinitis and atopic dermatitis. Scratch test results are: house dust 2+, mite 2+, cedar −, orchard grass 3+, and ragweed 2+. This subject breathes through her mouth only at night due to nasal occlusion. This subject has suffered from atopic dermatitis since infancy, and also had a pollen allergy since she was 22-23 years old. Her symptoms worsen from May to early July every year. During this period, she sneezes constantly and has a runny nose. She does not feel any effects from steroid nasal sprays, and only experiences a strong dryness sensation with a pain as local irritation symptoms.

As a trial, the BNP nasal solution with a concentration of 50 µg/ml obtained in Example 1 was sprayed only once into each nostril of this subject (the amount of BNP administered in one nasal cavity was 6.5 µg); then 10 min later, the BNP nasal solution permeated the nasal mucous membrane and the symptoms were relieved, and watery nasal drip was improved. Since these effects were confirmed, she went out under the sun after spraying once in the morning on the 2nd day, and symptoms of pollen allergy were improved to a barely-troublesome level, and runny nose and sneezing were not observed until early evening. For a period of 5 days thereafter, she used the 50 µg/ml BNP nasal solution spraying once in the morning; on some days runny nose and sneezing did not occur all day, but on other days runny nose occurred in the afternoon; in these cases, application twice a day could relieve the symptoms. Antihistamine drugs were not necessary. Moreover, local irritation symptoms did not occur.

Test Example 12 (Case 12)

The subject is a 21-year-old female who is a patient with moderate mixed-type rhinitis. She has a past history of atopic dermatitis, and her father suffers from allergic rhinitis. Scratch test results are: house dust 1+, mite 2+, cedar 3+, orchard grass 1+, and ragweed 1+. This subject has suffered from atopic dermatitis since infancy, and also pollen allergy since 2 years ago; she has itching with a tickling sensation and rhinorrhea, nasal occlusion, which worsen particularly when she is tired. Nasal occlusion is strong and she goes through mouth breathing several times a day. Nasal steroids did not show sufficient effects on this subject at times of worsening of the symptoms, particularly on rhinorrhea.

As a trial, the BNP nasal solution with a concentration of 50 µg/ml obtained in Example 1 was sprayed only once into each nostril of this subject (the amount of BNP administered in one nasal cavity was 6.5 µg); 10 min later, watery rhinorrhea stopped and opening of the nasal passages was slightly improved; nasal occlusion was improved 20 min later. The next morning, by only one spray, the usual nasal itching and runny nose were relieved after 10-20 min, and the nasal occlusion sensation reduced and the effects lasted until dinnertime. As a result of use twice a day in the morning and at night for one week, watery rhinorrhea and nasal occlusion were improved; accordingly the application was discontinued. Thereafter the effects lasted and rhinorrhea and nasal occlusion did not relapse for 4-5 days after the discontinuation of the nasal application, maintaining the relieved condition. The application of BNP nasal solution twice a day improved the symptoms from moderate to mild degree.

Test Example 13 (Case 13)

The subject is a 28-year-old female who is a patient with the most severe rhinorrhea-type rhinitis. She has a past history of atopic dermatitis, and her younger sister suffers from allergic rhinitis and atopic dermatitis. Scratch test results are: house dust 1+, mite 2+, cedar 3+, orchard grass 3+, and ragweed 2+. This subject has suffered from atopic dermatitis since infancy, and symptoms of pollen allergy began to appear since around 20 years of age. In particular, runny nose and sneezing became very severe from around June, and she constantly blew her nose all day and runny nose was discharging when she bent her head down. This subject rarely undergoes mouth breathing, but has a nasal occlusion.

The BNP nasal solution with a concentration of 100 µg/ml obtained in Example 1 was sprayed only once into each nostril of this subject (the amount of BNP administered in one nasal cavity was 13 µg); then 30 min later, runny nose stopped. Sneezing also stopped 1 hr after the application. Thereafter, the effects of the present nasal solution lasted for half a day, and it was around 9 o'clock in the evening when runny nose began to discharge again. The degree of improvement in symptoms by the present BNP nasal solution was from a severe to a mild level.

Upon application of steroid nasal solutions or internal application of steroids, the subject had irritation such that the surface of her nasal mucous membrane felt tightly-stretched, as well as dryness as side effects, and accordingly satisfactory therapeutic effects had not been obtained. In contrast, while the present BNP nasal solution shows superior effects to steroids, it does not exhibit such side effects.

Test Example 14 (Case 14)

The subject is a 46-year-old female who is a patient with most severe mixed-type rhinitis. She has a past history of atopic dermatitis and allergic conjunctivitis, and her child also suffers from allergic rhinitis. Scratch test results are: house dust 2+, mite 2+, cedar 3+, orchard grass 3+, and ragweed 2+. This subject has suffered from a runny nose, nasal occlusion and itching of the eyes since she was about 10 years old, and from the age of 20, rhinitis has become more severe and runny nose continuously discharged if the nostrils were not packed. This subject has a fairly strong nasal occlusion, and breathes through her mouth for a considerable amount of time a day.

The BNP nasal solution with a concentration of 50 µg/ml obtained in Example 1 was sprayed only once into each nostril of this subject (the amount of BNP administered in one nasal cavity was 6.5 µg); 5 min later, she felt that her nose became lighter, and that her nasal passages opened after 15 min, with a marked improvement observed for rhinorrhea; the nasal occlusion sensation was markedly improved 30 min later, and itching of the throat was relieved. The subject was deeply moved by the efficacy of the present nasal solution.

In addition, according to the report by the subject, steroid nasal solution showed not only irritation symptoms with a feeling of nasal dryness, but also no efficacy at all. In the case of the present nasal solution however, it gave a rather moist feeling.

By spraying once before bedtime, she slept well without nasal drip, without taking oral antihistamine drugs. With application before bedtime, rhinorrhea symptoms did not bother her during the daytime of the next day, blowing her nose only once every hour, and combined internal use of antihistamine drugs was not necessary. The effects lasted for 3-4 days by only one application before bedtime; thereafter, application of once before bedtime every 3-4 days, totaling 4 time applications, enabled maintenance of relieved conditions wherein rhinorrhea, nasal occlusion and itching of the eyes reduced to moderate levels. The degree of improvement in symptoms by the BNP nasal solution was from a most severe to a moderate level.

Test Example 15 (Case 15)

The subject is a 45-year-old female who is a patient with severe sneezing/rhinorrhea-type rhinitis. She has a past history of atopic dermatitis, and her child also suffers from atopic dermatitis and allergic rhinitis. Scratch test results are: house dust 2+, mite 3+, cedar 1+, orchard grass 2+, and ragweed 1+. This subject continuously has perennial watery nasal drip, but has almost no nasal occlusion. Nasal application of steroid drops increased watery nasal drip, giving strong nasal irritation.

The BNP nasal solution with a concentration of 200 µg/ml obtained in Example 1 was sprayed only once into each nostril of this subject (the amount of BNP administered in one nasal cavity was 26 µg); then 10 min later, nasal drip stopped. At this time, she reported that she had no local irritation symptoms or feelings of discomfort. Without combined internal application of antihistamine drugs, the effect of stopping nasal drip lasted all day. Watery nasal drip was suppressed by use once a day on the next day. The degree of symptoms was improved from severe to mild by the use of the BNP nasal solution for 2 days.

Test Example 16 (Case 16)

The subject is a 35-year-old male who is a patient with the most severe mixed-type rhinitis. He has a complication of allergic conjunctivitis, and his father, elder sister and child suffer from allergic rhinitis. Scratch test results are: house dust –, mite 1+, cedar 2+, orchard grass 3+, and ragweed 1+. This subject has continuous watery nasal drip, so that he has to use 2 boxes of tissue paper to blow his nose. He also has nasal occlusion, and is in the condition of complete nasal stuffiness the entire time. These symptoms have persisted from late May to September. When nasal steroids are applied, he tends to have steroid resistance, so that the effect of the steroids cannot be attained from the second time use; moreover, he has strong irritation to the use of steroids.

The BNP nasal solution with a concentration of 50 µg/ml obtained in Example 1 was sprayed only once into each nostril of this subject (the amount of BNP administered in one nasal cavity was 6.5 µg); then 10 min later, watery nasal drip, nasal itching, and nasal occlusion sensations were relieved. At this time, no irritation symptoms were observed. Subsequently, spraying once in the morning for 5 days resulted in disappearance of nasal itching 10 to 15 min later, and watery nasal drip stopped, and these effects lasted for one day without runny nose all day long. By use twice in the morning and at night, nasal occlusion was improved and internal use of antihistamine drugs became unnecessary. The degree of improvement in symptoms of a 5-day application period was from most severe to mild. After discontinuation of the usage, relieving effects of rhinorrhea and nasal occlusion were maintained for 7 days.

For comparison, tests were performed using ANP nasal solutions.

Example 7

Results of comparative examples using ANP preparations are summarized in Table 7, and details are described below as test examples 7-18.

TABLE 7

|  | Case 17 (comparative example 1) | Case 18 (comparative example 2) | Case 2 (comparative example 3) |
| --- | --- | --- | --- |
| Sex | Male | Female | Female |
| Age | 28 years old | 28 years old | 40 years old |
| Severity level | Severe | Severe | Severe |
| Disease type | Mixed | Mixed | Sneezing/rhinorrhea |
| Family history | Father; atopic dermatitis, allergic rhinitis | Mother; allergic rhinitis | Child; atopic dermatitis |
| Past history | Atopic dermatitis | Atopic dermatitis | Atopic dermatitis |
| Scratch test | House dust: 2+<br>Mite: 3+<br>Cedar: —<br>Orchard grass: 3+<br>Ragweed: 2+ | House dust: 2+<br>Mite: 2+<br>Cedar: 2+<br>Orchard grass: 3+<br>Ragweed: 2+ | House dust: 2+<br>Mite: 2+<br>Cedar: 2+<br>Orchard grass: 3+<br>Ragweed: 1+ |
| Diagnostic finding |  |  |  |
| Nasal drip (average number of nose blows a day) | Severe runny nose and sneezing (Approx. 20) | (11-20) | Nasal drip is severe, so that she uses a pile of tissue paper for nose blowing. (Approx. 20) |
| Nasal occlusion | Nasal occlusion sensation becomes strong in around June, so he has mouth breathing. | Strong at night. | No mouth breathing at all, but has nasal occlusion. |
| Effects of steroid nasal spray | — | Not used because of nasal irritation. | Nasal irritation, itching, sneezing and rhinorrhea conversely worsen, without subjective effects of improvement. |
| Dosage form | ANP nasal solution preparation | ANP nasal solution preparation | ANP nasal solution preparation |
| Dosage | 50 µg/ml | 50 µg/ml | 50 µg/ml |
| Number of nasal applications | Twice in the morning and at night | Twice in the morning and at night | Twice in the morning and at night |
| Number of days applied | 7 days | 2 days | 3 days |
| Symptom improvement by initial nasal application | The number of nose blows reduced to approximately 10 times a day, but runny nose and sneezing persisted, and nasal occlusion sensation was not improved. Tickling feeling of the nose improved slightly. | Rhinorrhea did not stop 15 min later, but at 20 min later she subjectively felt that nasal passages had opened wider than before the application. However, at 20 min thereafter, the nasal occlusion relapsed and she felt nasal itching. | At 1 hr later, a slight improvement in nasal itching was observed, but was not so apparent. Rhinorrhea was not improved. |
| Progress and symptom improvement | ANP nasal solution was used twice a day for 7 days; however, rhinorrhea and nasal occlusion were not improved compared to the state before the application. | On the next morning, nasal occlusion was so strong that she woke up due to the occlusion, and she sprayed the ANP nasal solution once, but nasal occlusion relapsed 20 min later. | After 3 days, only nasal itching was mildly improved, but the persistence was low, and when the ANP solution was used in the morning, the symptoms relapsed in the afternoon. No improvement in rhinorrhea was observed, and she needed to blow her nose approximately 20 times a day. |
| Symptom improvement | Severe → severe | Severe → severe | Severe → severe |

Comparative Example 1 (Case 17)

The subject is a 28-year-old male who is a patient with severe mixed-type rhinitis. He has a past history of atopic dermatitis, and his father suffers from atopic dermatitis and allergic rhinitis. Scratch test results are: house dust 2+, mite 3+, cedar −, orchard grass 3+, and ragweed 2+. This subject has suffered from atopic dermatitis since infancy, and symptoms of pollen allergy appeared since he began to work; nasal occlusion becomes strong particularly around June and he tends to breathe through his mouth. Runny nose and sneezing are severe, and the number of times of nose blowing is approximately 20 times a day.

The ANP nasal solution with a concentration of 50 µg/ml obtained in Example 1 was sprayed twice a day into each nostril of this subject (the amount of ANP administered in one nasal cavity was 6.5 µg); however, runny nose and sneezing did not stop and the nasal occlusion sensation was not improved. The ANP nasal solution was used twice a day for 7 days, but no changes in rhinorrhea and nasal occlusion were observed between before and after the application, indicating no improvement. The degree of improvement in symptoms was from severe before the ANP application to still severe after the ANP application.

Comparative Example 2 (Case 18)

The subject is a 28-year-old female who is a patient with severe mixed-type rhinitis. She has a past history of atopic dermatitis, and her mother also suffers from allergic rhinitis. Scratch test results are: house dust 2+, mite 2+, cedar 2+, orchard grass 3+, and ragweed 2+. This subject has perennial persistent rhinitis, which particularly worsens between early summer and early autumn, with constant sneezing and watery nasal drips, and a strong nasal occlusion at night. She reported that she does not use steroids because of nasal irritation.

The ANP nasal solution with a concentration of 50 μg/ml obtained in Example 1 was sprayed only once into each nostril of this subject (the amount of ANP administered in one nasal cavity was 6.5 μg); rhinorrhea did not stop 15 min later, but 20 min later she subjectively felt that nasal passages opened compared to the condition before application. However, thereafter within approximately 20 min, nasal occlusion re-occurred, and she had a tickly sensation. The ANP nasal solution was re-sprayed once at the night of the same day, and she subjectively felt that nasal passages opened 20 min later, but nasal occlusion re-occurred with a tickly sensation 15 min after the re-spraying. On the next morning, nasal occlusion was so strong it woke her up, so she sprayed the ANP nasal solution once; however, 20 min later nasal occlusion re-occurred. The severity level and the degree of improvement were from severe to severe, showing no satisfactory improvement effects.

Comparative Example 3 (Case 2)

The subject is the same subject as the Case-2 subject in whom 100 μg/ml CNP nasal solution was tested. However, she was 40 years old when the ANP nasal solution was tested, because 11 months had passed since the CNP nasal solution was applied for 3 days. Background information including past history, family history, scratch test results, effects of steroids, etc. are the same as those described in test example 2 and Table 4.

The ANP nasal solution with a concentration of 50 μg/ml obtained in Example 1 was sprayed once into each nostril of this subject (the amount of ANP administered in one nasal cavity was 6.5 μg); however, no immediate effect was observed. One hour later, a sign of slight improvement in nasal itching was observed, but it was not clear, and rhinorrhea was not improved. The ANP nasal solution was applied on the night of the same day, in the morning and at night of the next day and the day after the next day similarly to that mentioned above; 3 days later, only nasal itching was slightly improved, but its persistence was short, and nasal itching re-occurred in the afternoon when the nasal solution was used in the morning. No improvement in rhinorrhea was observed by application for 3 days, and she needed to blow her nose approximately 20 times a day. The severity level and degree of improvement was from severe to still severe, showing no apparent improvement effects.

Summary of the Results of Case Studies

As is clear from the above test examples, the nasal solutions of the present invention manifested their effects, at approximately 10 to 20 min after spraying, on the representative symptoms of rhinitis, i.e., nasal occlusion, sneezing attack and rhinorrhea. They are effective to any type of rhinitis including the mixed type, the nasal-occlusion type, and the sneezing/rhinorrhea type. Furthermore, the nasal solutions of the present invention including both the CNP nasal solutions and the BNP nasal solutions not only have remarkable effects of improvement in rhinitis, but also their manifestation of drug efficacy is extremely fast, i.e., they are fast-acting, without local side effects such as irritation and systemic side effects such as drowsiness. They are also long-lasting, with excellent compliance of application of only 1-2 times a day. Thus, the present nasal solutions have ideal characteristics as nasal drop preparations. In addition, a trend was observed that repeated applications result in an increase in the degree of improvement in some cases.

The nasal solutions of the present invention have more significant effects than those of conventional steroids and antihistamine drugs, and they are revolutionary drugs in terms of persistence, in that they can relieve symptoms by application only once a day.

Moreover, since ANP and BNP share the same receptors, they were presumed to have identical effects; surprisingly, however, only BNP had significant effects of the two, contrary to expectations.

We have conducted similar clinical tests with additional 10 cases; as a result, extremely remarkable improvement effects of symptoms were observed in all the cases including many severe cases wherein internal administration of anti-allergic agents and steroids could be terminated thereby, it is worth noting that with the nasal solutions of the present invention, a drastic reduction in medical expenses can be expected, in addition to their significant drug efficacy.

INDUSTRIAL APPLICABILITY

The therapeutic preparations for rhinitis of the present invention are extremely effective for the treatment of various types of rhinitis, in particular allergic rhinitis, without a concern of causing side effects; thus, the present preparations are applicable to patients in whom conventional steroid nasal sprays and antihistamine drugs are not effective, or patients who must avoid the use of these drugs due to possible side effects, as well as young patients.

Meanwhile, regarding the treatment of cedar pollen allergy, and for patients with moderate to most severe cedar pollen allergy, the following treatment is recommended according to the Allergic Rhinitis and Its Impact on Asthma (ARIA), 2008 edition: the treatment should start with a steroid nasal spray alone, then the amount of the steroid nasal spray should be increased when no improvement is observed; and an antihistamine drug should be added for sneezing/nasal itching, ipratropium bromide hydrate should be added for rhinorrhea, and a vasoconstrictive agent or an oral steroid should be added to nasal occlusion; that is, a step-wise treatment is recommended.

However, conventionally-used steroid nasal sprays are used with a frequency of 2-4 times a day for adults, of which effects only last fora short period and the time required for manifestation of the effects is 1-3 days or more, requiring about 2 to 4 weeks before the maximum level of effects is reached. The level of satisfaction with the effects is low. In addition, they have side effects such as nasal irritation, dryness, and irritation in the throat, headache, and a risk of complication with infections due to long-term use.

Mometasone furoate hydrate, which has an advantage of spraying once a day, has become recently available in Japan; however, the effects reported on pollen allergy in Europe and the United States after 2 weeks of application are as follows: the degree of improvement in overall symptoms was 40-50%, the degree of improvement in nasal occlusion was 30-40%; thus, they are not sufficient from the viewpoint of therapeutic effects.

In contrast, the therapeutic preparations for rhinitis of the present invention can markedly improve severe rhinitis symptoms by application only once a day, without internal administration of steroids and antihistamine drugs. In addition, the effects are fast-acting and long-lasting. Namely, manifestation of the effects can be observed immediately after the application, and in most cases both nasal occlusion and rhinorrhea are markedly improved 10-20 min after the application. Moreover, in all the cases, excellent improvement effects on nasal occlusion and rhinorrhea are maintained all day by only spraying once or twice a day.

Furthermore, local side effects observed in steroid nasal sprays are not at all manifested, and all the subjects reported that the present preparations are used quite comfortably. Systemic side effects such as drowsiness and a decrease in working efficiency observed by internal administration of antihistamine drugs and steroids are not present. Moreover, they have good compliance because their administration frequency is one spray at once or twice per day. Namely, the therapeutic preparations for rhinitis of the present invention are superior over conventional nasal solutions in terms of the fast-acting and long-lasting properties, are without side effects and have a good compliance; therefore they have ideal characteristics as a therapeutic preparation for allergic rhinitis.

Accordingly, practical application of the therapeutic preparations for rhinitis of the present invention is very promising as a novel therapeutic preparation for rhinitis that replaces conventional steroids and antihistamine drugs.

The invention claimed is:

1. A method of treating rhinitis, the method comprising applying a composition that comprises an effective amount of C-type natriuretic peptide (CNP) to a nasal cavity or nostril of a subject in need of such treatment, wherein the CNP is selected from the group consisting of CNP-22 and CNP-53, wherein the amino acid sequence of CNP-22 is SEQ ID NO: 1 and the amino acid sequence of CNP-53 is SEQ ID NO:22.

2. The method of treating rhinitis according to claim 1, wherein the concentration of the CNP is 20-200 µg/g weight of the composition.

3. The method of treating rhinitis according to claim 1, wherein the concentration of the CNP is 50-200 µg/g weight of the composition.

4. The method of treating rhinitis according to claim 1, wherein the concentration of the CNP is 50-100 µg/g weight of the composition.

5. The method of treating rhinitis according to claim 1, wherein the rhinitis is infectious rhinitis, hypersensitive non-infectious rhinitis, irritant rhinitis, atrophic rhinitis, or specific granulomatous rhinitis.

6. The method of treating rhinitis according to claim 5, wherein the infectious rhinitis is acute rhinitis or chronic rhinitis.

7. The method of treating rhinitis according to claim 5, wherein the hypersensitive non-infectious rhinitis is combined-type rhinitis (hypersensitive nose), rhinorrhea-type rhinitis, congestive-type rhinitis, or dry-type rhinitis.

8. The method of treating rhinitis according to claim 7, wherein the combined-type rhinitis (hypersensitive nose) is allergic rhinitis.

9. The method of treating rhinitis according to claim 8, wherein the allergic rhinitis is allergic rhinitis against at least one allergen selected from the group consisting of house dust, mite, cedar, orchard grass, ragweed, and cat hair.

10. The method of treating rhinitis according to claim 5, wherein the irritant rhinitis is physical irritant-induced rhinitis, chemical irritant-induced rhinitis or radiation-induced rhinitis.

11. The method of treating rhinitis according to claim 1, wherein the rhinitis is atrophic rhinitis or specific granulomatous rhinitis.

12. The method of treating rhinitis according to claim 1, wherein the rhinitis is mixed-type rhinitis, sneezing/rhinorrhea-type rhinitis, or nasal-occlusion-type rhinitis.

13. The method of treating rhinitis according to claim 1, wherein the composition is selected from an ointment preparation, a gel preparation, a cream preparation, a lotion preparation, a liquid preparation, a powder preparation or a spray preparation.

14. The method of treating rhinitis according to claim 13, wherein the composition is selected from a gel preparation, a liquid preparation or a spray preparation.

15. The method of treating rhinitis according to claim 1, wherein the rhinitis is rhinitis in a subject suffering from atopic dermatitis.

16. The method of treating rhinitis according to claim 1, wherein the rhinitis is rhinitis with treatment resistance to steroids.

17. The method of treating rhinitis according to claim 1, wherein the rhinitis is rhinitis in a subject having a difficulty in withdrawal from steroids.

18. The method of treating rhinitis according to claim 1, wherein the rhinitis is rhinitis with treatment resistance to antihistamine drugs.

\* \* \* \* \*